(12) United States Patent
Kriesel et al.

(10) Patent No.: US 11,124,596 B2
(45) Date of Patent: *Sep. 21, 2021

(54) ADHESIVE VISCOELASTOMER AND ITS USE IN STABILIZED STORAGE CONTAINERS

(71) Applicant: Tak Logic LLC, Ettrick, WI (US)

(72) Inventors: Matthew Wayne Kriesel, Melrose, WI (US); Troy Bradley Goodenough, Mindoro, WI (US)

(73) Assignee: Tak Logic LLC, Ettrick, WI (US)

( * ) Notice: Subject to any disclaimer, the term of this patent is extended or adjusted under 35 U.S.C. 154(b) by 312 days.

This patent is subject to a terminal disclaimer.

(21) Appl. No.: 15/731,815

(22) Filed: Aug. 7, 2017

(65) Prior Publication Data
US 2019/0002623 A1    Jan. 3, 2019

Related U.S. Application Data

(63) Continuation-in-part of application No. 14/999,722, filed on Jun. 20, 2016, now Pat. No. 10,807,767.

(60) Provisional application No. 62/231,004, filed on Jun. 22, 2015.

(51) Int. Cl.
| | |
|---|---|
| *C08G 18/48* | (2006.01) |
| *C08G 18/10* | (2006.01) |
| *C08G 18/70* | (2006.01) |
| *C08G 18/28* | (2006.01) |
| *C09J 171/00* | (2006.01) |
| *C09J 191/00* | (2006.01) |
| *C09J 4/00* | (2006.01) |
| *C08G 59/16* | (2006.01) |
| *C08G 18/22* | (2006.01) |
| *C08G 18/76* | (2006.01) |
| *A61B 50/33* | (2016.01) |
| *A01K 97/06* | (2006.01) |
| *B05D 1/02* | (2006.01) |
| *B65D 25/04* | (2006.01) |
| *B65D 33/06* | (2006.01) |
| *C09J 175/08* | (2006.01) |
| *C09D 175/08* | (2006.01) |
| *C08K 5/00* | (2006.01) |
| *A61B 50/00* | (2016.01) |
| *A61B 50/30* | (2016.01) |
| *C08G 18/36* | (2006.01) |

(52) U.S. Cl.
CPC .......... *C08G 18/4841* (2013.01); *A01K 97/06* (2013.01); *A61B 50/33* (2016.02); *B05D 1/02* (2013.01); *B65D 25/04* (2013.01); *B65D 33/06* (2013.01); *C08G 18/10* (2013.01); *C08G 18/227* (2013.01); *C08G 18/283* (2013.01); *C08G 18/4812* (2013.01); *C08G 18/4825* (2013.01); *C08G 18/4829* (2013.01); *C08G 18/4845* (2013.01); *C08G 18/70* (2013.01); *C08G 18/7671* (2013.01); *C08G 59/1472* (2013.01); *C09D 175/08* (2013.01); *C09J 4/00* (2013.01); *C09J 171/00* (2013.01); *C09J 175/08* (2013.01); *C09J 191/00* (2013.01); *A61B 2050/002* (2016.02); *A61B 2050/3008* (2016.02); *C08G 18/36* (2013.01); *C08G 2390/40* (2013.01); *C08G 2650/36* (2013.01); *C08K 5/0016* (2013.01)

(58) Field of Classification Search
CPC ............ C08G 18/4841; C08G 18/4812; C08G 18/4825; C08G 18/7671; C08G 18/4829; C08G 18/227; C08G 59/1472; C08G 18/283; C08G 18/70; C08G 18/10; C08G 18/4845; C08G 2390/40; C08G 2650/36; C08G 18/36; C09J 4/00; C09J 191/00; C09J 171/00; C09J 175/08; C08K 5/0016; A61B 50/33; A61B 2050/002; A61B 2050/3008; A01K 97/06; B05D 1/02; B65D 25/04; B65D 33/06; C09D 175/08
See application file for complete search history.

(56) References Cited

U.S. PATENT DOCUMENTS

| | | | |
|---|---|---|---|
| 3,507,071 A * | 4/1970 | Newton | ................. A01K 97/06 43/57.1 |
| 5,677,413 A | 10/1997 | Barksby et al. | |
| 5,864,001 A | 1/1999 | Masse et al. | |
| 6,588,511 B1 | 7/2003 | Kriesel et al. | |
| 6,673,409 B1 | 1/2004 | Wheatley | |

(Continued)

*Primary Examiner* — Rabon A Sergent

(74) *Attorney, Agent, or Firm* — M. Paul Hendrickson; Bryan R. Rosiejka

(57) ABSTRACT

The invention provides a unique thermoset viscoelastomeric reaction product and a container combination comprised of the supportive base equipped with a thermoset viscoelastomer reaction product possessing unexpectedly superior adhesive and cohesive efficacy rendering it especially useful as an adhesive insert in a container combination. The thermoset insert bonds to any suitable supportive structure. The unique viscoelastomeric reaction product inserts adhesively immobilize items placed thereupon and adhesively or permanently bonds to most conventional containers. The tenacious cohesive and adhesive features of the insert allows for inverted stowage of stowed items. Due to the confining adhesive and cohesive attributes of the insert, structural supports of a flexible or solid base without a conventional confining structure provide a unique container combination for the stowed items. Containers equipped with the unique insert also surprisingly provide an aseptic environment especially useful for hygienic applications.

69 Claims, 5 Drawing Sheets

(56) References Cited

U.S. PATENT DOCUMENTS

| | | |
|---|---|---|
| 6,896,065 B2 | 5/2005 | Kriesel et al. |
| 7,041,719 B2 | 5/2006 | Kriesel et al. |
| 7,125,602 B2 | 10/2006 | Wheatley |
| 7,252,867 B2 | 8/2007 | Wheatley |
| 7,910,188 B2 | 3/2011 | Wheatley |
| 7,923,088 B2 | 4/2011 | Wheatley |
| 8,110,269 B2 | 2/2012 | Wheatley |
| 8,110,270 B2 | 2/2012 | Wheatley |
| 8,302,213 B2 | 11/2012 | Kriesel |
| 9,974,342 B1 | 5/2018 | Kriesel |
| D880,950 S | 4/2020 | Kriesel et al. |
| 10,681,830 B1 | 6/2020 | Goodenough |
| 10,717,582 B1 | 7/2020 | Goodenough |
| 10,807,767 B1 | 10/2020 | Kriesel et al. |
| D902,584 S | 11/2020 | Kriesel et al. |
| 10,914,087 B1 | 2/2021 | Kriesel et al. |
| 2004/0191446 A1 | 9/2004 | Kriesel |
| 2004/0200623 A1 | 10/2004 | Kriesel |
| 2006/0272367 A1 | 12/2006 | Kriesel |
| 2006/0287147 A1 | 12/2006 | Kriesel |
| 2008/0005929 A1 | 1/2008 | Hardy et al. |
| 2008/0026658 A1 | 1/2008 | Kriesel |
| 2008/0250729 A1 | 10/2008 | Kriesel |
| 2009/0042676 A1 | 2/2009 | Kriesel |
| 2010/0170139 A1* | 7/2010 | Zhou ................ A01K 97/06 43/54.1 |
| 2012/0222457 A1 | 9/2012 | Kriesel et al. |
| 2015/0053583 A1 | 2/2015 | McCormick et al. |

\* cited by examiner

ADHESIVE VISCOELASTOMER AND ITS USE IN STABILIZED STORAGE CONTAINERS

CROSS-REFERENCE TO RELATED APPLICATION

This application is a Continuation-in-Part of U.S. Non-provisional application Ser. No. 14/999,722 filed Jun. 20, 2016 which is a non-provisional application of U.S. Provisional Application No. 62/231,004 filed Jun. 22, 2015, all of which applications are incorporated herein by reference in their entirety.

FIELD OF INVENTION

The present invention relates to a highly cohesive and adhesive thermoset viscoelastomeric reaction product and stabilized storage containers, and more particularly to storage containers equipped with inserts of the reaction product which securely maintain and release stowed items at their original placement.

BACKGROUND OF THE INVENTION

Inserts for commonly used compartmentalized storage containers, such as for kitchen appliances, toolboxes, tackle boxes, desk drawers, etc. often rely upon non-slip rubber inserts or adhesively backed VELCRO type fasteners to retain stowed items in an orderly manner. The VELCRO fastener system requires a dual adhesive attachment to the item to be retained and to the container itself. Other means for retaining objects to containers include molded cavities or other mechanical retention means such as clamps, straps, coverings, clips, etc. designed to mechanically restrain an item within the container. Unfortunately, none of these container retention systems have effectively solved an age-old problem of effectively retaining stowed items in their originally stowed position. Too frequently, such retention systems, upon use or aging, become broken or inoperable for practical use.

The age-old problem of orderly maintaining items stored in a container as originally stowed is well illustrated by the common use of fishing tackle boxes filled with fishing equipment, such as fishing lines, hooks, leaders, lures, etc., which upon use often leads to a snarled and entangled mess of fishing equipment. As a result, the angler often devotes precious fishing time to tediously untangling and prepping the desired fishing equipment. The disarray of tackle box items occasionally leads to personal injury, such as an inadvertent hooking injury.

It is practically impossible to maintain an orderly tackle box under its common environmental usage. Too frequently, the fishing tackle boxes are roughly handled or placed in an inverted transport position or roughly transported, which inherently causes the disarray. Boating to a fishing site will frequently create conditions inherently leading to a disarray of fishing tackle box contents. This often arises due to wind, boating waves, etc. typically encountered as the fishing boat speeds to the fishing site. Numerous attempts to solve this age-old problem have remained unsuccessful. A common practice of placing non-slip rubber mats in each of the individual tackle box compartments fails to correct the problem since the mats or compartments provide little, if any, protection against displacement of stowed tackle box equipment.

From a practical standpoint, most tacky adhesives lack sufficient adhesiveness and cohesiveness to effectively restrain items, while others lack essential cohesive and adhesive stability for stowage use. Another heretofore unknown problem associated with any releasable adhesive hinges upon adhesive stability of the adhesive material under pressurized adhesive conditions. A further problem associated with such common adhesives results from an inability to retain substantially the same degree of adhesiveness upon an adhered stowed item over an extended stowage period. Certain adhesives lose adhesiveness, while others convert into a permanent adhesive rendering it virtually impossible to subsequently remove a stowed item that is adhesively bonded thereto. There exists a need for a unique adhesive composition which would serve as a stabilized adhesive stowing insert which retains a substantially constant degree of adhesiveness and cohesiveness when used as an insert for stowing items over extended stowage periods. There further exists a need for a container insert which actually maintains a stowed item at its original stowed positon even if the item is stowed in an unorthodox position. Unexpectedly, it has been discovered pursuant to the present invention that a unique thermoset cohesive and adhesive viscoelastomeric reaction product, when fabricated into a stowing insert, provides a powerful and substantially constant degree of adhesiveness and cohesiveness so as to positionally retain and release a stowed item over prolonged stowage periods.

The present invention solves the perplexing age-old problem of effectively retaining articles in their original stowed position for subsequent use by virtue of a unique container insert derived from a unique thermoset reaction product, which may be bonded to the container, or which can serve as an adhesive insert between the contacting surfaces of the container and a stowed item. Consequently, items placed within the container will remain in their original immobilized position under a substantially stabilized adhesive attraction by the insert, notwithstanding subsequent physical or environmental mishandling. Thus, for example, when an angler arrives at the fishing site, everything within a tackle box equipped with the unique insert will remain as originally placed for instant retrieval and use.

There accordingly has existed a long standing need for a unique adhesive composition useful in the manufacture of a unique bonded or removable insert possessing powerful cohesiveness and adhesiveness (or bonding attraction) to a container wall (e.g., top, ceiling, sidewall, bed walls, etc.), as well as to a wide variety of items placed for stowage therewithin. It would be of further great benefit if the adhesive composition and the insert compositionally possessed an inherent cohesiveness throughout its entire compositional make-up. There also exists a need for a unique adhesive and cohesive thermoset insert, which upon extended use, may be cleansed of interfacing adhesively clogging debris (e.g., dirt, dust, grime, etc.) simply by removing the insert from the container and washing with common household detergents to restore its surface adhesiveness. There further exists a commercial need for a self-cohesive insert which possesses sufficient adhesive tenaciousness to rigidly retain adhered articles placed thereupon, but will also allow the articles to be removed therefrom without damaging or breaking the article. There further exists a need for a cohesive and adhesive insert, which upon release of the stowable item, will separate cleanly without leaving any polymeric residue upon the separated stowed item. Further unbeknownst would be an insert possessing antimicrobial properties so as to provide an aseptic stowing environment. Unexpectedly, the unique cohesive and adhesive attributes of the thermoset elastomeric reaction product and container inserts provided by this invention uniquely solve these long-standing needs.

BRIEF SUMMARY OF THE INVENTION

The present invention provides a unique thermoset viscoelastomeric reaction product, which when used as an insert for containers, creates a container with an unexpectedly superior ability to stow items. In contrast to containers fitted with non-slip inserts or other mechanical restraining systems, the present invention provides a unique thermoset viscoelastomeric reaction product having self-cohesive and adhesive properties having particular usefulness as an insert for stowage containers. These inserts, derived from a viscoelastomeric reaction product, uniquely possess an inherent internal cohesiveness, as well as an adhesive attraction to the container walls and most stowable items. Consequently, the cohesive and adhesive inserts, as provided by this invention, possesses a unique interfacial adhesive attraction to the container itself, as well as to the objects placed thereupon for stowage. Unlike conventional non-slip rubber type inserts which fail to possess any appreciable adhesive attributes, the cohesive and adhesive inserts herein will typically compositionally possess an adhesive attraction of more than 300 grams of force ($g_f$) per square centimeter ($cm^2$) of contact area, as ascertained by a constant test speed pulling force needed to separate a thermoset viscoelastomeric reaction product test patch from a 1.76 $cm^2$ circular nickel plated test probe at 20° C. These unique adhesive attributes are well suited to maintain a sufficient adhesive attraction to securely maintain stowed items adhered thereto against any further inadvertent movement until a sufficient counteracting force is applied to break the adhesive bonding between the stowed item and the viscoelastomeric insert. Since the inserts are based upon a viscoelastomeric reaction product possessing powerful inherent adhesiveness and cohesiveness properties, they are also prone upon extended use to lose their surface adhesiveness over time by an external surface contamination of debris accumulation, such as dust particles, dirt, grime, etc. The thermoset viscoelastomers of this invention may be provided in a removable insert form for container usage which permits contamination cleaning by conventional washing techniques, such as placing the contaminated inserts in a conventional household dishwasher and washing the inserts with conventional household dish washing detergents. If desired, the inserts may be permanently bonded to the container by thermoset bonding thereto.

The present invention provides a unique thermoset viscoelastomeric reaction product possessing extraordinary cohesiveness and adhesiveness useful in solving the age-old problem of maintaining an orderly arrangement of retrievable stowed items within the confinement of a container. The embodiments of the invention are particularly applicable for use in a stabilized container combination comprised of a container equipped with an insert of the thermoset viscoelastomeric reaction product possessing an unexpectedly superior adhesiveness to the container walls (including sidewalls, bed and top walls) while also tenaciously adhesively retaining and immobilizing an item emplaced upon the insert. Surprisingly, the inserts obtained from the thermoset viscoelastomeric reaction product also possess unique antimicrobial properties. The viscoelastomer, and inserts fabricated therefrom, compositionally possess these unique adhesive, cohesive and antimicrobial properties throughout their entire viscoelastomeric thermoset structure. The viscoelastomeric reaction product, and inserts thereof, may be conveniently provided as removable sheets (e.g., inlays or liners), or essentially as permanent coatings, tenaciously bonded to the container walls (e.g., floor or bed, side walls and top walls) of the stowing container. Since the thermoset viscoelastomeric compositions used herein inherently possess a highly tacky, adhesive and cohesive structure, the viscoelastomeric insert in a removable form will also remain tenaciously adhesively bonded to the container, as well as to stowed items placed thereupon. The adhesion characteristics of the insert, however, do not permanently immobilize an item placed in contact therewith, but will adhesively disengage (without leaving any cohesive polymeric residue) by the application of a sufficient pulling force to disengage the stowed item from the thermoset insert. These unique cohesive and adhesive thermoset viscoelastomer characteristics permit a disengagement of those items placed upon the insert, as well as a selective removal of the insert from the container. The cohesive and adhesive characteristics are extremely stable against cohesive and adhesive degradation. The adhesiveness of the insert towards a stowed item remains substantially unchanged over prolonged stowage conditions. When used as an insert, the container interface is typically of a greater total surface contact area than the stowed object placed thereupon, which results in a stronger adhesive attraction at the stowing container interface than the articles placed thereupon. Accordingly, the total contacting surface of the insert, which interfaces onto the stowing container, will generally exceed the overall contacting surface to the stowed object. Consequently, a total lesser adhesive force will exist at the item contacting surface than at the container wall interface. Alternatively, the interfacing section may be essentially permanently bonded to the container.

DETAILED DESCRIPTION OF THE INVENTION

Figure 1:
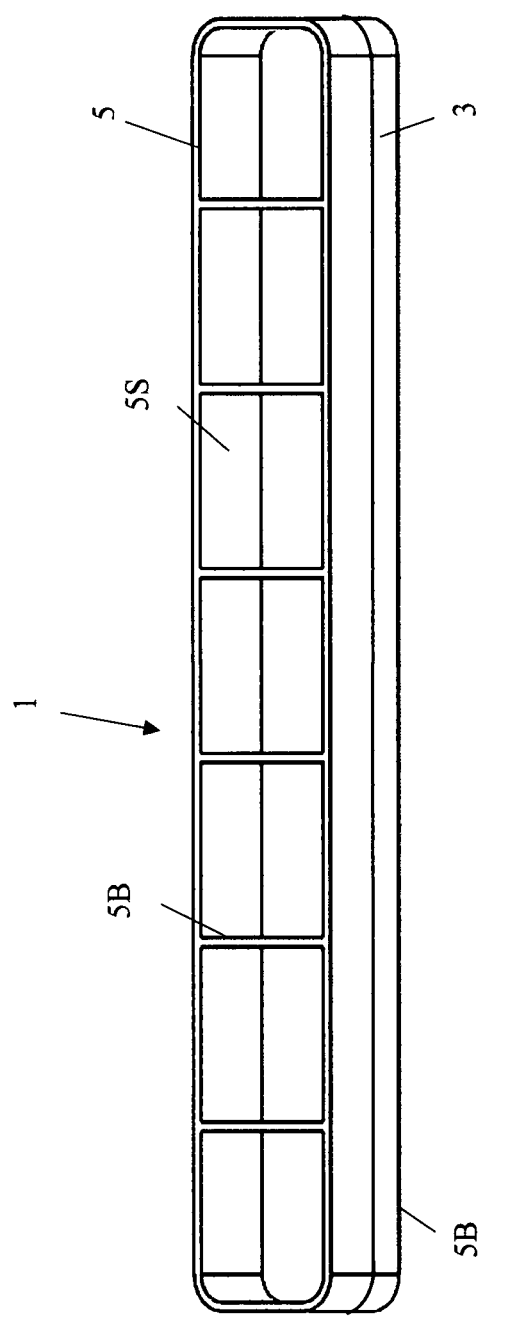
FIG. 1 is a perspective top view showing a stabilized container combination comprised of a transparent container equipped with a thermoset viscoelastomeric insert of this invention.

With reference to FIGS. 1-5, there is provided pursuant to this invention a unique thermoset viscoelastomeric reaction product useful for use in a stowing container combination 1 equipped to uniquely stabilize emplaced articles or items 20 upon an insert 3 at a fixed stowable and stabilized emplacement position. This unique container combination 1 generally comprises a supportive base 5 equipped with the unique cohesive and adhesive thermoset viscoelastomeric insert 3 derived from the reaction product which provides a first adhesive interfacial surface section by adhesively adhering, or by being bonded by thermosetting, to the supportive base 5, and an opposing adhesive surface positioned to adhesively engage and adhere onto a stowed article emplaced thereupon. It has been unexpectedly discovered that the cohesive and adhesive thermoset viscoelastomers, and the inserts 3 derived therefrom, create powerful and unique intermolecular cohesive and adhesive forces in what appears to be a localized intrinsic adhesive polarity charge or attraction, which in turn provides an unexpectedly superior stowing adhesive efficacy when used as a container insert 3. Compositionally, the cohesive and adhesive viscoelastomeric insert 3 effectively serves to stabilize and immobilize items or articles 20 against subsequent dislodgement until manually removal from the insert 3. The stowing container combination 1 needs only a base support 5 of either a rigid or flexible construction in order to contain stowed items 20, since the exceptional cohesive and adhesive viscoelastomeric properties of the insert 3 serve to effectively restrain the items 20 adhesively placed upon the supportive base 5 against any further movement.

Within the field of cohesive and adhesive materials, it has been found that there exists a very limited class of thermoset viscoelastomeric reaction products which meet the necessary prerequisite properties for use as inserts 3 as provided herein. Amongst the unique attributes most suitable for use as an insert 3 are:

1. a releasable adhesiveness which tenaciously clings onto an adhered stowed item 20, but will cleanly and cohesively release from an adhered item 20, without flaking or leaving residue, upon application of a counterforce sufficient to overcome the adhesive attraction between the stowed item 20 and the insert 3;
2. a soft textured viscoelastomer which serves to embed an adhered item 20 within its adhesively engaging structure;
3. a viscoelastomer material having a substantially uniform cohesiveness throughout its entire compositional makeup providing a relatively high tensile strength which permits an adhesive embedding of an adhered item 20 with a clean cohesive separation therefrom when removed;
4. an adhesive material, which upon use, may be cleansed of adhering contaminants that adversely affect its adhesive efficacy;
5. a substantially stable insert 3 which retains a substantially stable degree of adhesiveness when stowing items 20 over prolonged storage periods; and
6. a thermoset viscoelastomeric reaction product and insert characterized as having an adhesive adherence to stowed items 20 of more than 300 $g_f/cm^2$.

The insert 3 must compositionally possess a tenacious cohesiveness and adhesiveness in the form of a highly localized adhesive attraction to items 20 placed upon the insert 3. Normal usage is typically effectuated by a slight pressing of the stowable item 20 against the insert 3, which in turn causes an indentation and embedding of the item 20 within the insert 3, along with a concomitant increase in overall interfacial contact area and an apparent localized intermolecular adhesiveness therebetween. Basically, the softer textured adhesive elastomers (e.g., soft rubber type adhesives), and particularly the thermoset viscoelastomers which possess the aforementioned prerequisite cohesiveness and adhesiveness properties, along with releasable attributes, may be used for this purpose.

Due to the fluid flow characteristics of the thermoset reaction product under stress and its thermoset structure, the polymeric materials most suitably useful as inserts 3 in the combination 1 embrace those commonly referred to as a viscoelastomers. The thermoset viscoelastomeric reaction product and suitable inserts 3 for use herein broadly embrace a class of thermoset viscoelastomeric reaction products characterized as having a sufficient pliable character to embed stowed items 20 within its contacting surface area, and a sufficient cohesive and adhesive attraction to tenaciously adhere to items 20 placed upon its surface, while also remaining substantially intact upon the removal of the stowed item 20 from the insert 3. Within the vast field of thermoset viscoelastomers, the newly discovered thermoset viscoelastomers have been found to possess surprisingly superior cohesiveness and adhesiveness, rendering them most effective for use as inserts 3 herein. The unique stowing efficacy provided by the unique container combinations 1 fitted with the unique thermoset viscoelastomeric inserts 3 accordingly rests upon the unique cohesiveness and adhesiveness which the viscoelastomeric insert 3 compositionally and intrinsically provides to the combination 1. It has been further observed that the viscoelastomeric insert 3 possesses an exceptional stability against any substantial cohesive or adhesive change over prolonged stowing time periods, as well as uniquely providing antimicrobial properties.

Particularly effective are a novel class of thermoset viscoelastomeric reaction products which unexpectedly possess a releasable but highly powerful cohesive and adhesive efficacy. Molecularly, the thermoset viscoelastomeric reaction products apparently possess superior intermolecular cohesiveness and adhesiveness, which renders the viscoelastomeric reaction product uniquely adaptable for use as a releasable insert 3 herein. The creation of such a unique thermoset viscoelastomeric reaction product and the inserts 3 derived therefrom compositionally involves providing a cured viscoelastomeric molecular structure which significantly contributes towards an increase in the adhesive tack as exerted by the insert 3 upon stowable items 20 coming into contact with its strong adhesive surface. This effect may be accomplished by creating a thermosetting reaction media which compositionally favors the development of a highly cohesive and adhesive thermoset viscoelastomeric reaction product for use as an insert 3. The cured reaction media provides not only unexpectedly superior cohesive and adhesive attraction properties, but also other unique attributes, which are significantly beneficial to the stowable container art. Apparently, the molecular makeup of the viscoelastomer and the unique adhesive and cohesive attributes of the inserts 3 will, upon engagement to an emplaced item 20, provide an interfacing surface characterized as having apparent surface asperities and/or protuberances which effectively allow for an increase in the total area of contact between the item 20 and the insert 3. This phenomena, in combination with a powerful adhesiveness and an embedding of the item 20 within the insert 3 (e.g., as due to its viscoelastomeric properties), results in an unexpectedly powerful adhesive bonding and restraint of the item 20 to the insert 3. In general, the adhesive bonding of the item 20 to the insert 3 may actually be substantially greater than the gravitational forces exerted upon the item 20 itself, as evident by an adhesive retention of an item 20 by the insert 3 even when the adhered item 20 is inverted to an upside-down gravity defying position.

The viscoelastomeric thermoset composition is derived from a unique thermosetting reaction media containing a cohesive mass of plasticizing agents structurally supported by a thermoset polymerizate which provides an appropriate polarized level of molecular cross-linkage and bridging of straight chain linkages within the thermoset viscoelastomeric reaction product. The subsequently cured chemical viscoelastomeric thermoset derived from such a unique reaction media possesses a uniquely superior adhesive ability to cling onto contacting articles or items 20 with an intrinsic cohesive property, which when properly fabricated, can selectively release adhered objects or items 20 therefrom by applying an outwardly pulling force sufficient to overcome the tenacious adhesive forces bonding the item 20 to the viscoelastomeric thermoset insert 3. The adhesive separation breaks cleanly without leaving any residue since the thermoset viscoelastomer inherently possesses sufficient internal cohesiveness to tenaciously retain its structural integrity.

Figure 2:
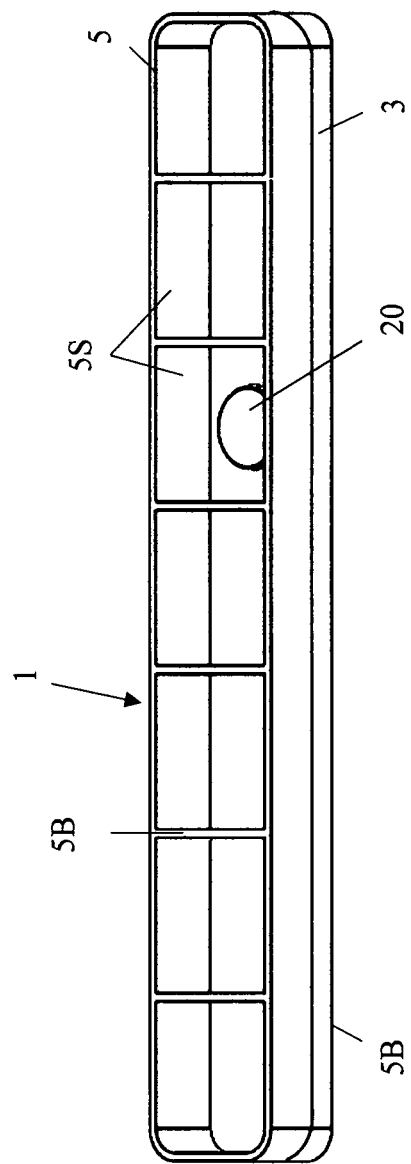
FIG. 2 is a perspective frontal view showing the container combination of FIG. 1 in which one of the compartments contains a medicinal pill.
Figure 3:
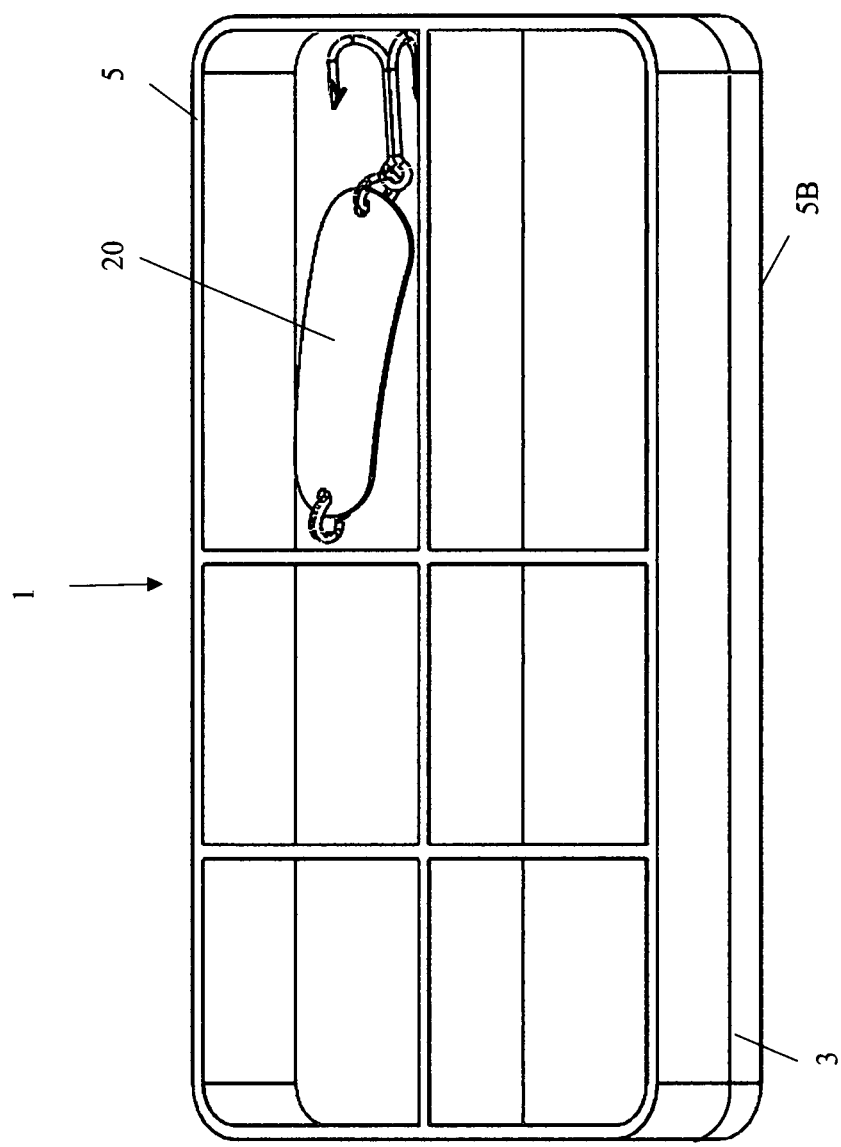
FIG. 3 is a partial perspective view showing a stabilizing container combination of this invention depicting a stowed fishing lure.

The unique embodiments of the thermoset viscoelastomer insert 3 and the stabilized stowing container combinations 1 herein are illustrated in FIG. 3 in the form of a transparent compartmentalized fishing tackle container (generally prefixed as a container 5) and in FIGS. 1-2 as a pill box container 5 equipped with compartmentalized sections 5S having a container bed 5B fitted with an antimicrobial, adhesive and cohesive thermoset viscoelastomeric insert 3, which may be a removable insert or a tightly bonded insert 3 securely affixed by thermosetting to the supportive base 5 shown as a container 5. In the combination 1, the larger surface contact area of the viscoelastomeric insert 3 will typically provide a greater adhesive attraction to a supportive base 5 (depicted as a container bed 5B) than the lesser total surface contact area typically afforded by an item or object 20 stowed thereupon. In contradistinction to conventional prior art containers typically equipped with rubber liners which serve only as non-slip liners to prevent surface slippage of stowed articles 20, the inserts 3 of this invention atypically tenaciously adhesively adhere onto stowed articles 20 emplaced thereupon and retain their original emplacement orientation over prolonged stowage. The inserts 3 provided herein have been found to possess such an unexpectedly high order of adhesiveness so as to restrain an adhered article from dislodgement even when the container 5 with the adhered article 20 is placed in an inverted position. Surprisingly, such a gravity defying phenomenon applies to hefty stowed articles 20, such as a heavy solid stainless steel dinner knife 20 or household scissors, which would normally be expected to be readily dislodged from the insert 3 when placed in an inverted position.

Since these thermoset viscoelastomeric inserts 3 characteristically possess a flexible structure, they are readily adaptable for use in combination with a supportive base 5 of a flexible structure as well as those of a solid support construction 5. Due to the unique and superior cohesive and adhesive efficacy of the viscoelastomer, the thermoset viscoelastomeric inserts 3 may be provided in any form which provides sufficient support and interfacial surface contact so as to adhere (physically or chemically) to a host of supportive substrates 5 (i.e., a supportive base) including the sidewalls 5W, top walls (not shown) and bed walls 5B of a container 5, as well as flexible substrates 5 such as used in sporting goods, and flat surface supports (e.g., countertops, trays, benches, tables, etc.), while also providing a sufficient interfacial adherence to any item 20 so as to confine or immobilize any item 20 placed in contact therewith. The necessary interfacial adherence of the thermoset elastomeric insert 3 to a container structure (e.g., 5W, 5B, etc.) and stowable item 20 may be effectuated by providing an insert 3 of sufficient size to immobilize those items or articles 20 desired to be stowed by the stabilized container combination 1.

The thermoset viscoelastomeric reaction product may be suitably manufactured under unique thermosetting reaction media conditions in which the necessary thermosetting precursors of polymerizable reactants are immersed in a lipophilic plasticizing media, which upon curing, provides the desired thermoset viscoelastomeric reaction product which is especially suited for use as the viscoelastomeric thermoset insert 3 herein. In procedures which involve a reaction media thermoset bonding of the insert 3 to the container 5, the uncured thermosetting reactants may be applied by spray coating, injection molding, casting, etc. at a desired thickness to the desired container substrate (e.g., walls 5W or container compartments 5S) and then allowed to cure in situ to provide a coated thermoset viscoelastomeric insert 3 which then may become essentially permanently bonded to the container 5. The amount of plasticizer and the level of cross-linking precursors in the reaction media can change the cured bonding characteristics. This technology may be applied to the most commonly available containers 5 (e.g., metal and non-metal containers such as wood, cloth, thermosets and thermoplastics, etc. types of containers). By applying the uncured reactants to the desired container sections (e.g., beds 5B, walls 5W, including top walls, etc.), the uncured thermoset viscoelastomeric insert coating 3, when cured, becomes more firmly bonded to the container surface and may be used to provide a permanently bonded coating. Conventional flaming techniques to prepare a thermoplastic surface for coating may be applied to improve the bonding.

The uncured thermosetting reactants may accordingly be directly deposited (e.g., sprayed, injected, molded, casted etc.) onto any suitable flexible or solid supportive base 5 (e.g., container beds 5B and walls 5W) and allowed to cure into the desired thermoset bonded elastomeric insert or coating 3. Thus, the uncured thermosetting reactants may be applied and cured as coatings, strips, systematic castings (e.g., circles, spirals, etc.) or in any other fabricating form sufficient to create a thermoset viscoelastomeric insert 3 of a sufficient size to hold or immobilize the intended items 20 to be placed thereupon. Injection molding, extrusion, spraying, vacuum molding, blading, spreading and other conventional thermosetting coating techniques may be used to apply the uncured reactants to the container walls (i.e., top walls, sidewalls and/or bed wall) as well as in the manufacture of prefabricated insert sheets adaptable for use as a removable insert 3. The curing rate and flow characteristics (viscosity) of the uncured reactants can be effectively controlled by the type and amount of catalytic agents, reactants, thermal conditions, plasticizers, etc. used in conducting the thermosetting reaction. Excellent viscosity control during the initial uncured prefabrication stages may be achieved, for example, by increasing the level of lower molecular weight plasticizers and a decrease of the higher molecular weight plasticizer (e.g., such as ESO) concentration.

The thermoset viscoelastomeric inserts 3 herein are particularly applicable for use to most portable or handled containers and may be prefabricated for use as an insertable or removable insert 3. Such removal inserts may be prepared by conventional calendaring, sheeting, molding, etc. of the uncured thermosetting reactants applied onto a suitable substrate at the desired insert thickness, which upon curing, may be subsequently cut to fit the desired compartmentalized container sections 5S.

The fishing tackle and medicinal pill boxes 5 of a transparent construction as shown in FIGS. 1-3 embody several unique embodiments of the invention. In the FIGS. 1-3 depictions, the sheet-like construction of the interfacing thermoset viscoelastomeric insert 3 are shown as resting upon the container bed 5B within compartmentalized container units 5S of a fishing tackle box and a pill box container 5. If desired, the adhesive character of the major interfacing surface for item 20 contact may be altered so as to more readily release an adhered item 20 while still maintaining adequate adherence to the bed 5B of the container 5. Such surface changes may be implemented by providing a bottom surface of a greater surface area which adheres to the bed 5B as a substantially flat or smooth insert surface, whereas the upper surface may be an irregular surface containing pronounced ridges and valleys designed to substantially reduce its surface contact area with the item 20 and its concomitant cohesiveness. This is generally unneeded since the container insert 3 interface area will typically exceed the stowed item interfacing surface contact area. Since the insert 3 inherently possesses a powerful cohesiveness and tensile strength, a substantially greater separating force will be required to overcome the cohesive and adhesive bonding of the insert 3 to the container 5.

Compositionally, the self-adhering inserts 3 as used herein differ from the conventional non-slip type of liners such as the commonly used thermoplastic rubber inserts, etc., which normally require an adhesive adjunct or other adhesive coating in order to satisfactorily adhere to a container surface. Unlike such conventional inserts, the thermoset viscoelastomeric inserts 3 as used herein possess powerful cohesiveness throughout their entire compositional structure so as to retain structural integrity upon separation from an adhered item 20, while also tenaciously adhering until released to most of the common metals, thermosets, and thermoplastic containers (both solid or flexible), as well as most stowable articles. The cohesive molecular components of the inserts 3 are tenaciously and inherently bound throughout their entire compositional make-up rendering them virtually impossible to leave any compositional residue when an adhesively viscoelastomeric insert 3 is separated from a container 5, or upon a removal of a stowed item 20 from the insert 3. Since the highly adhesive inserts 3 (as provided herein) possess unusually high adhesive bonding efficacy comparative to any commonly known and available adhesive materials, they may be effectively used as a top ceiling or sidewall insert 3 for both solid or flexible containers 5. The inserts 3 tenaciously and uniquely adhere to the stowed items 20, as well as to a conventional container 5, which unique attributes permit a horizontal, vertical and inverted stowage of items 20.

The insert 3 may be appropriately tailored so as to adhesively fit a particular compartmentalized section 5S of a container 5. There exist special benefits for certain combinations 1 provided by a removable insert 3. This will permit a removal of the insert 3 from the container 5 for cleaning, repositioning, etc. This constitutes a major advantage for many of the container combinations 1 and especially for those equipped with small stowing compartment sections 5S. As illustrated by Example 3, the removable insert 3 may be provided in a consumer friendly form which allows the consumer to purchase an insert 3 adapted for insertion and use in a used stowing container, since the cohesive and adhesive inserts 3 securely adhere to a host of objects 20 which come into direct contact therewith. The thermoset viscoelastomeric cohesive insert 3 also tends to accumulate dust, dirt, linen, and other contaminates coming in contact with its exposed surface. Excessive accumulations of such contaminants can dramatically reduce the adhesive efficacy of the exposed external surface of the thermoset viscoelastomeric insert 3 to the extent it no longer possesses a sufficient capacity to effectively stabilize and immobilize objects 20 placed upon its interfacing surface. By providing a thermoset viscoelastomeric interfacing section or insert 3 of the container combination 1 in a removable or washable form (e.g., a film, sheet, etc.), any foreign matter clogging its adhesive efficacy may accordingly be readily removed and restored to an effective cohesive and adhesive use by washing. Uniquely, the accumulation of such unwanted foreign matter upon the thermoset viscoelastomeric insert 3 surface area may be effectively removed by simply washing the insert 3 with common soaps and water, such as by simply washing the insert 3 in a conventional dish washer with common dishwashing soaps so as to restore its adhesive efficacy. The superior cohesiveness of the viscoelastomeric reaction product and the insert 3 allows for washing under conditions which would often cause other materials to disintegrate. The removable insert 3 form thus provides certain useful advantages over the permanently bonded thermoset insert 3 form, and vice versa. It is therefore evident that for certain end uses, the removable insert 3 (e.g., bulky containers with highly compartmentalized small open surface areas) is best suited whereas the thermoset bonded form for access friendly flexible or washable containers 5 may best serve the combination 1. Commonly, hand toted solid container combinations 1, such as illustrated by the Figures, as well as other flexible container combinations 1, may benefit by the thermosetting of reaction media to the supporting base 5.

Although the providing of the viscoelastomeric insert 3 as an insertable and removable liner 3 can be desirable for ease of cleaning, the uncured viscoelastomeric reactants when cured in situ upon the walls 5W or bed 5B of a restraining container or receptacle 5 will create a tenacious and permanent, and possibly a chemical bonding, therebetween. For many container combinations 1, the thermoset bonded form (i.e., curing to the supportive base 5) may be more desirable than a removal form. Permanent boding of the insert 3 to the walls 5W or bed 5B of a flexible container (e.g., backpacks, medical handbags, purses, duffel bags, sport shirts, hunting jackets, etc.) provides a combination 1 which may also be readily cleansed by washing the entire container combination 1, including the supportive container 5 with the insert 3 being permanently bonded or thermoset bonded thereto, without any concern over insert 3 disintegration. For other applications wherein the supportive surface affords a sufficient flat, open surface area to permit the insert surface to easily be washed and cleansed from air borne and other contaminants, the thermoset bonding of the insert 3 to the container 5 may be most desirable. Since compositionally the insert 3 provides antimicrobial protection, the insert 3 becomes particularly useful should microbial contamination become a major concern to a particular combination 1 of its use. Since the antimicrobial component exists throughout the entire insert 3, it cannot be removed by washing.

The term "stowing container combination 1" as used herein refers to the combination of the insert 3 and any supportive structure 5 which in the stowing container combination 1 collectively provides a confining and stowing environment for a stored item 20 contained by the stowing container combination 1. The stowing container combination 1 may include conventional sidewalls, compartments and covers, but may become unneeded for many applications, such as in stowing trays. The ability to eliminate conventional confining structures arises because of the uniquely powerful cohesive and adhesive properties of the insert 5. The insert 3 may be in a prefabricated coating form (continuous or discontinuous) or by sheathing, molding, film, slab, sheet, casting or any other prefabrication forming method which takes advantage of its cohesive and releasable adhesive features in the combination 1. As previously mentioned, the insert 3 may interface onto any supportive structure 5 essentially as a permanent or thermoset bond thereto (e.g., in situ curing) or as a removable liner 3 relying upon the powerful cohesive and adhesive characteristics of the insert 3. Since the adhesiveness of the thermoset viscoelastomeric insert 3 serves to confine an adherent item 20 emplaced thereupon, the stowing container combination 1 may solely rely upon an open, flat supportive platform structure 5 so as to avoid the need for conventional compartmentalized containers or other conventional container restraints. Accordingly, flat and open supportive structures 5, such as a tray, in combination with the insert 3, uniquely provides the containing or confining container combination 1 for stowed items 20.

Figure 4:
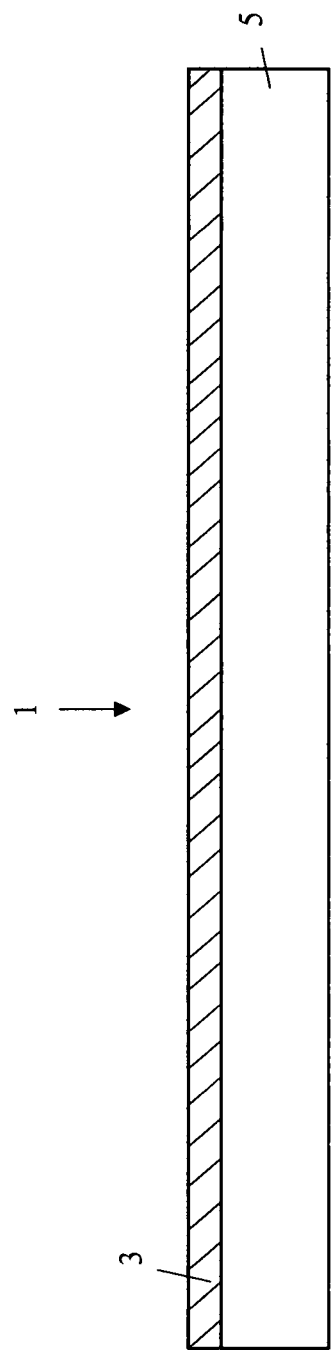
FIG. 4 is a schematic cross-sectional view showing a tray coated with a stabilizing insert coating.

For certain combinations 1, as illustrated by the schematic cross-sectional tray depiction of FIG. 4, the thermoset viscoelastomeric insert 3, when used in combination with a flat surfaced supportive substrate such as in a tray 5 or even as a flexible substrate 5 fitted with the insert 3, the insert 3 itself provides the confining mechanism for the stowing container combination 1 without necessitating any other further confining means such as conventional confining sidewalls or covers. The thermoset viscoelastomeric insert 3 thus adhesively bonds or chemically bonds to any adhesive compatible supportive base structure 5. The insert 3 effectively serves as a means to confine and stow an item 20 placed upon any suitable supportive base surface 5 without the need of any other confining structure to retain the item 20. Unlike conventional trays which typically require a physical restraint in order to restrain stowed items from unwanted dislodgement, the inserts 3 provided herein by themselves serve as a powerful confining or restraining element for the stowed article 20 held in confinement within the combination 1. Thus, any insert compatible supportive base 5 in combination with the unique thermoset insert 3 provides the confining container 1 for the confined stowage of items 20. The ability to contain stowed items 20 in a vertical or even an inverted position upon a flat supportive surface 5 or an open flexible or supportive surface 5 without needing any confining walls or other containment factor creates a unique innovation for the container industry. Due to its cohesive and adhesive efficacy of the viscoelastomeric insert 3, the need for a raised edge, rim or cover for a flat surfaced container combination 1 (e.g., such as trays) accordingly becomes unneeded.

Due to its adhesiveness, the inserts 3 are prone to adhere to microbes as well as stowable items 20. The usefulness of the insert 3 becomes particularly applicable within the hygienic field such as typically arises in the common usage of dental and medical trays to retain stowable items 20 at medical and dental clinics, hospitals, examining rooms, etc. The inherent antimicrobial or aseptic properties of the insert 3 render it highly effective for a vast array of medical and other hygienic uses. Surgical trays, examining room trays, dental and dental hygienist trays, etc. equipped with the insert 3 to stow hygienic devices 20 afford a unique ability to immobilize surgical, medical and dental instruments placed thereupon while also providing a surprising and unexpected effective aseptic and sterile environment. Due to the unique antimicrobial properties of the thermoset viscoelastomeric insert 3 herein, the capacity to adhesively engage and stow medical and dental instruments in a sterile and aseptic environment represents a significant advance over the current hygienic state of the art. This is particularly significant since conventional adhesive materials lacking antimicrobial attributes in an unprotected environment create an unacceptable increased health hazard which common and unavoidable hazard is unexpectedly and effectively alleviated by the insert 3. The permanency of the thermoset bonding, or its removable features, and exceptional viscoelastomeric insert 3 tack or adhesive efficacy without needing further confinement, plus its antimicrobial properties, affords a significant innovative advance over the current state of the hygienic art.

The manufacture of the insert 3 in an unbounded form may be prepared by initially depositing the uncured thermosetting elastomeric reactants in a suitable reaction media and prefabricating form (e.g., compartmentalized sized sections, or sheeted, etc.), such as by casting, injection molding, calendaring, or by simply depositing measured amounts of the uncured flowable reactants upon a moving chemically inert belt (equipped with or without heating), etc. and thereafter allowing the uncured reactants to cure under manufacturing conditions adapted to form the thermoset viscoelastomeric insert 3 of the desired thickness and form. Upon curing in a desired calendared, strip, sheet, casted, etc. form, the cured thermoset viscoelastomeric reaction product may suitably be cut or sized to an appropriate configuration to match its desired container combination 1. Inserts 3 of the desired configuration and thickness may also be prepared by conventional molding techniques (e.g., injection molding). For certain applications, the appropriate uncured, flowable reactant dosage as needed to provide the desired insert configuration and coating thickness may be directly applied to the container 5, which then upon subsequent curing, creates the desired stabilized container combination 1. In the uncured thermosetting form, the thermoset reaction media can be formulated (e.g., epoxidized soybean oil to ester plasticizer levels) so as to provide the desired flow or viscosity characteristics so as to permit the casting, molding, etc. of an interfacing coated section or insert 3 of a desired configuration and thickness.

The present invention may be broadly adapted to a broad range of stowing container combinations 1. Combinations 1 designed for stowage of items 20 weighing a gram or less to those weighing a pound or more, all of which may be effectively stabilized and confined at their original stowed placement position. Notwithstanding the exceptional adhesive properties of the unique inserts 3 herein, the degree of adhesive immobilization exerted upon any item 20 placed upon the insert 3 will have a direct correlation to the total contacting surface area of the insert 3. A greater interfacial surface contact area with the stowed item 20 generally leads to a greater total adhesion to items 20 so as to allow a placement for larger and heavier items 20 thereupon. The heavier and bulker items 20 may require thicker inserts 3 than those used to stow lighter items 20. The adhesive characteristics or strength may vary over a wide range, rendering it possible to match a desired degree of adhesiveness to a desired end use. The cohesive and adhesive inserts 3 used herein will characteristically possess sufficient viscoelastomeric properties which allow the stowed item 20 to be embedded or cradled by the insert 3 as opposed to merely compressing without any appreciable item 20 embedding, as is the case for hard rubber inserts. In addition to providing a sufficient degree of cohesiveness and adhesiveness, the inserts 3 used herein must necessarily provide a relatively high degree of cohesive and adhesive stowing stability. This adhesive stability is evident in that the adhesive attraction reaches 90% of its maximum adhesive tack within one minute after a stowed item's 20 initial contact with the insert 3.

The utilization of the thermoset viscoelastomeric inserts 3 provides a unique cohesive and adhesive environment, creating strong cohesive and adhesive forces, which lead to unexpectedly superior stowing advantages of the thermoset viscoelastomeric insert 3 over any other known container insert. Conventional rubberized container inserts merely compress with a substantial and concomitant volume loss due to its compression. In contrast, when an item 20 is placed upon the viscoelastomeric insert 3 with a normal amount of applied placement pressure to adhesively engage onto the item 20, there will arise a concomitant counteraction of a fluidized flow by the insert 3, which in effect embeds the stowed items 20 within an adhesive cavity, thus creating a substantially greater contacting interface and adhesive attraction area than would normally arise by the simple tangential surface contact of a rubberized insert. It has also been observed that the adhesive attractive forces of the insert 3 will increase slightly after initial item 20 contact with the insert 3 and then stabilize. This same phenomena even applies when an item 20 is quiescently placed upon the insert 3, which placement may have a lesser initial adhesion release strength, but with time will ultimately become stabilized to a comparable adhesive value as the pressure applied item 20. The unique and atypical stowed item adhesive environment, as provided by the viscoelastomeric inserts 3 herein, coupled with their superior adhesive efficacy, create a stowing combination 1 possessing unheralded adhesion and adhesive stabilization upon stowed items 20 which were heretofore deemed unfeasible. Such an unheralded adhesive insert 3 advance allows for an uncanny confinement of a stowed item 20 in a horizontal or inverted position within the container combination 1.

The unique cohesiveness and adhesiveness of the insert 3 may be partly attributable to manner in which these viscoelastomeric inserts 3 inherently embed, cradle and adhesively engage a stowed item 20, coupled with their apparent extremely powerful adhesive attractive influence upon the stowed article 20. Conventional elastomers generally compress unilaterally about an impinging article and unilaterally rebound upon decompression so that the resting article tends to primarily rest tangentially upon the conventional elastomer. In complete contrast, an article 20 placed upon the viscoelastomeric insert 3 herein causes a displacement of the viscoelastomer, while partially submerging into the surrounding viscoelastomeric mass, without any substantive volumetric loss to the insert 3 (as opposed compression of a conventional rubber elastomeric mass). This creates an embedded cradle for the stowed item 20 while also applying an equalized pressure and adhesive attraction upon the stowed item 20. The cradling caused by the viscoelastomeric insert 3 exerts a uniquely uniform and powerful fluidized embedded and adhesive attractive force upon the embedded article 20. It may accordingly be logically concluded that the viscoelastomeric insert 3 inherently imparts a significantly greater adhesive attraction when items 20 are adhesively embedded within the viscoelastomeric insert 3 for stowage.

The initial embedding by forcible placement of the item 20 onto the viscoelastomeric insert 3 seems to create an indentation of a significantly greater surface contact area and a fluidized adhesive environment which does not normally occur in a compressive force against an ordinary elastomeric mass. This initiating contact establishes a deep-seated adhesive and stabilized viscoelastomeric attraction subject to a stabilized increase in adhesion, which in combination with what appears to be a molecular polar alignment within the cured thermoset viscoelastomeric reaction product, exerts an extremely powerful adhesive attractive force upon the stowed item 20. By physical analogy it much easier to entrap an item by an encompassing cupping and fluid-like entrapment under a superior attractive adhesive forces than to adhesively entrap and engage an item by tangential contact. It has also been further observed that pressure applied upon a stowable item 20 to more deeply embed the item 20 within the insert 3 can cause a concomitant increase in the initial adhesive bonding force of the item 20 to the insert 3 by a factor of ten percent (10%) as opposed to a quiescent placement. However, the quiescent placement of an item 20 upon the insert 3 will ultimately stabilize to a comparable adhesive separation value as when pressure has been applied to item 20. Evidently, there exists internal forces within the thermoset viscoelastomeric reaction product which creates this delayed increase in adhesiveness.

The surface area of the insert 3 facing the stowed object must also necessarily possess a releasable surface tack or adhesiveness which allows for an adhesive release of an item 20 placed thereupon as opposed to a permanent or temporary adhesive bonding between the article 20 and the insert 3. Commonly stowed items 20 weighing substantially more than conventional fishing tackle lures, such as carpentry or mechanical tools as commonly stowed in tool boxes, can also benefit from a container combination 1 appropriately fitted with the unique stabilized adhesive and cohesive insert 3, which may be specifically tailored-made to meet its intended use. The tailoring of the adhesive value involves the extent of cross-linking and polyether linkage within the thermoset polymeric structure, coupled with the amount and type of plasticizer provided within the thermoset viscoelastomeric reaction product. Moreover, the insert 3 must also provide a stable adhesive bonding without exhibiting any appreciable adhesive change over prolonged stowage conditions. Surprisingly, the inserts 3 as provided by this invention retain a substantially unchanged degree of adhesive bonding after stabilization with respect to items 20 stowed by the insert 3 over prolonged storage periods (e.g., 4 weeks or more). There typically exists less than a ten percent (10%) adhesive change after the initial stowing contact of the item 20 with the insert 3.

Figure 5:
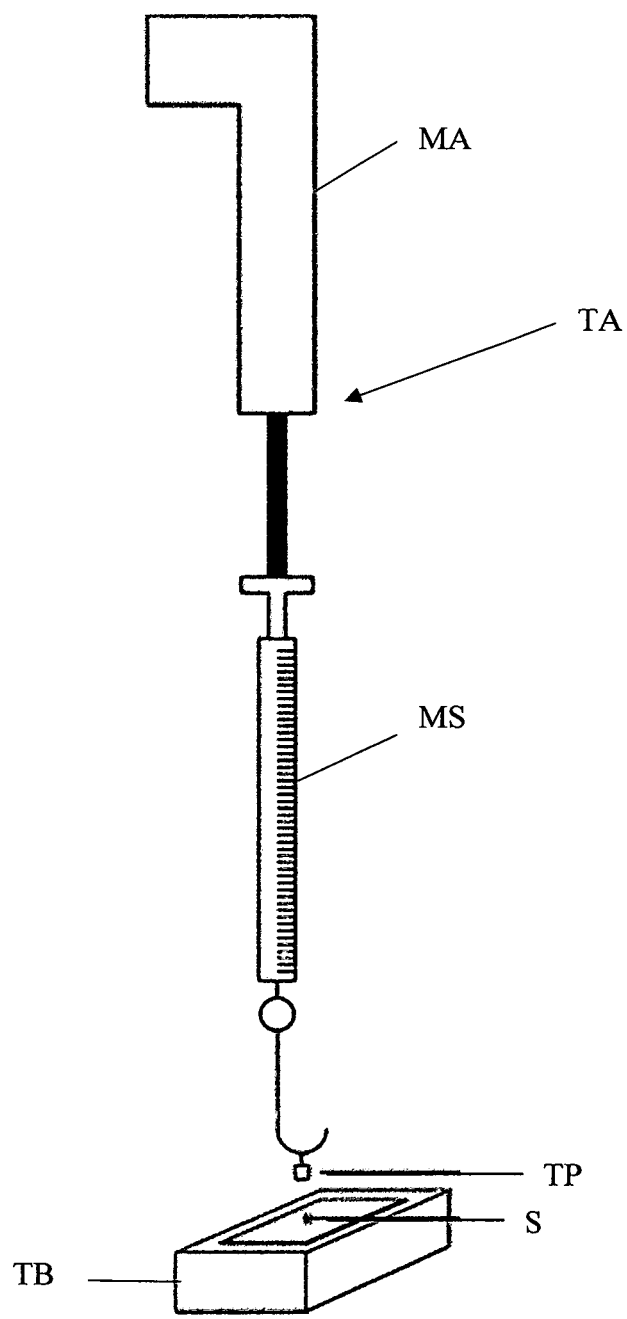
FIG. 5 is a schematic drawing showing an adhesion testing apparatus which may be used to test the cohesive and adhesive efficacy of the thermoset viscoelastomeric reaction product and inserts.

In contrast to conventional non-slip and rubber container inserts, the present inserts 3 typically exhibit an adhesion release strength of more than 300 g/cm$^2$ (grams force per centimeter square) as needed to overcome the adhesive attraction between the insert 3 and the emplaced item 20 as determined by the FIG. 5 testing apparatus. If desired, inserts 3 exhibiting about a threefold (900 g/cm$^2$) to about a six fold (1800 g/cm$^2$) or more in an adhesive release strength may be obtained. Combinations 1 possessing the unique stowage characteristics for most uses will exemplarily embrace inserts 3 having an adhesive bonding strength of more than 400 g/cm$^2$, usually more than 500 g/cm$^2$, but most generally less than about 1200 g/cm$^2$, and especially those inserts 3 having an adhesive release or separation strength ranging from about a 500 g/cm$^2$ to about a 1000 g/cm$^2$. Even though the thermoset viscoelastomeric reaction product may be tailored too much higher releasable adhesiveness (e.g., greater than 1200 g/cm$^2$), the excessive adhesiveness can render it particularly difficult to release the item 20 from the container combination 1. On a most practical use range, about 600 to about 1000 g/cm$^2$ represents a highly effective insert 3 usage range. The higher adhesive values become more difficult to manually separate and will tend to merge into the permanent adhesive range. However, for certain applications, such as using the thermoset viscoelastomeric reaction product to securely ground a gaming apparatus to a grounded support (e.g., game play equipment, supportive posts, equipment anchoring, etc.) may make it desirable to utilize a reaction product of about 1500 to about 2200 g/cm$^2$ or higher adhesion and separation value.

As mentioned, the stowing container combination 1 need not be a rigid structure. Flexible stowing container combinations 1, such as flexible medical equipment containers, first responder tote bags, flexible photographic equipment containers, tool bags, fishing tackle bags and a host of other container types of a flexible construction 5 may benefit from the unique stowage attributes afforded by this invention. Since the thermoset viscoelastomeric insert 3 tenaciously adheres to items 20 placed thereupon, the container combination 1 does not necessarily require traditional sidewalls or covering lids. Unlike conventional stowing containers, which necessarily need to store stowed items in an upright position, the inserts 3 uniquely allow for storage of items 20 in an inverted or horizontal position without any substantial loss of adhesive attraction to the inverted item 20 over a prolonged storage time. Such surprising stowing attributes are indicative of the unique cohesive and adhesive stability provided of a container combination 1 fitted with the cohesive and adhesive viscoelastomeric thermoset insert 3, and the equivalents thereof, as provided by this invention. The viscoelastomeric properties of the insert 3 will also provide stowed item 20 protection against impact damage.

In another embodiment of the invention as illustrated by FIGS. 2-4, the thermoset viscoelastomeric insert 3 may be utilized to impart a desired aseptic effect to the stowing container combination 1. As illustrated by FIG. 2, the compartmentalized pill boxes 5 for stowing medicinal pills are effectively aseptically protected from microbes through the use of an antimicrobial thermoset viscoelastomeric insert 3, which constitutes an inherent property of the thermoset viscoelastomeric reaction product. The pill box insert 3 inherently provides powerful aseptic properties to the container combination 1 and stowed items 20. Thus, when the interfacing viscoelastomeric insert 3 (e.g., as a coating, sheet, film, layered section, etc.) is applied to a container wall 5W or bed 5B, both the exposed outer surface and the inner container interfacing surface abutting onto the insert 3 will inherently benefit from its unique anti-microbial properties. The thermoset viscoelastomeric insert 3 and its surrounding environment accordingly do not foster microbial growth, but rather inhibit the development of unhealthy microbial or fungal infestations. Accordingly, the use of the thermoset polymeric insert 3 for surgical and medical uses, as well as other hygienic uses, coupled with the inherent self-cohesive and uniform antimicrobial properties throughout its entire mass, opens a new vista for aseptic sterilization which uniquely distinguishes the insert 3 from any other conventional insert. Accordingly, medical and other hygienic containers 5 for retaining hygienic items 20 under aseptic conditions, such as essential to the hygienic use of dental, medical or hygienic cabinet drawers and compartments, bags, kits, boxes, including pill boxes, as well as flat surfaced combinations 1 such as surgical, examining, medical and dental trays, etc. all of which will typically include a supportive base 5 interfacing onto and supporting the antimicrobial thermoset viscoelastomeric inserts 3. Such a stowing container combination 1 exhibits unexpectedly superior and unique antimicrobial advantages over the current technology by maintaining an orderly, aseptic, sterile and systematic environment for a stabilized placement of sterile medical instruments, devices and medicinal compositions, etc., all of which fulfills a long sought medical and hygienic need. As mentioned herein, should dust and other debris (including air borne particle contaminates sanitized by the insert 3) clog the adhesive surface of the thermoset elastomeric insert 3, the insert 3 may be readily restored to its original or native condition by a soap and water wash without adversely affecting its deep seated antibacterial, antifungal, adhesive and cohesive properties, which uniformly permeate throughout the entire compositional makeup of the insert 3, and those items 20 coming into contact therewith. Similar to medicinal and dental applications, unwanted infections arising from germ infested fishing hooks and lures may also benefit through the use of the insert 3. Thus, the thermoset viscoelastomeric inserts 3 are particularly well suited for a host of hygienic uses. Medical, dental and other hygienic combinations 1, such as used by First Responders, ambulance personnel, dentists, dental hygienists, physicians, surgeons, nurses, etc., are accordingly beneficially and uniquely bestowed with a superior self-sanitizing container combination 1 for stowing self-contained items 20 in a stabilized, immobilized, sterile and orderly environment.

If desired, the uncured insert reactants may be formulated so as to provide a transparent insert 3 which permits locating indicia, labels, decals, written messages such as item use or other desired instructions, etc., which are clearly visible through the transparent insert 3. Coloring additives such a pigments, dyes, etc., may also be formulated into the uncured reaction media to provide a desired coloring effect. The insert 3 may similarly be color coded to identify the stowed items 20 to be immobilized within the confinement of the combination 1. Similarly, fragrances may also be formulated into the uncured reactants to provide a scented insert 3. If desired, the insert 3 may also be externally utilized to cohesively and adhesively retain stacked or otherwise arranged containers 5 in an orderly fashion. If desired, identifying coded coloring indicia may be incorporated into the insert 3 to identify the respective contents of each container 5 or compartment 5S of the combination 1.

The insert 3 has a broad range of adhesive affinity to most customary containers 5, as well as to most stowable items 20, which broadly embraces a wide range of diverse stowed items and supportive containers 5. Accordingly, the insert 3 may be used to physically adhere or chemically bond a host of supportive bases 5 and items 20. The supportive base 5 may be illustratively constructed of a wide range of diverse materials, such as cellulosic materials (e.g., wood, wood composites, vegetative materials, etc.), thermosets, thermoplastics, plastic composites, metals (e.g., aluminum, steel, tin, metal alloys, etc.) textiles, glass and a host of other adhesive compatible rigid or flexible supportive materials 5. Accordingly, the stowing container combination 1 broadly applies to any supportive base 5 adhesively compatible with the insert 3. Certain of the halogen containing polymers (e.g., PVC) for certain formulations are adhesively incompatible with the adhesive properties of the thermoset viscoelastomeric inserts 3 herein. This may be due to the electronegativity of the PVC and the thermoset viscoelastomeric reaction product, which causes a repelling of like charges. Such non-adhesive PVC materials may, however, be effectively used as continuous and non-reactive manufacturing belts for use in the curing and prefabricating of molded, sheeted, filmed, casted, etc., inserts 3.

The insert 3 in its thermoset viscoelastomeric form may be appropriately provided as non-toxic, environmentally green friendly, and virtually free from residual gases or volatizing gases. The insert 3 may also impart impact and vibration absorbing attributes which further serves to protect stowed objects 20 from impact and vibrational damage. Accordingly, fragile stowed items 20, such as a photographic lens, electronic equipment, circuit boards, glass items and other delicate items 20, etc. may be protectively housed and/or restrainingly immobilized against impact damage and injury. The viscoelastomeric reaction product may also be effectively combined as a coating insert 3 with a foamed rubber to provide a protective stowing wrap combination for protecting fragile items 20. The thermoset viscoelastomeric insert 3, as desirably used in the container combination 1, will typically be less than 4 mm in thickness and more typically less than 3 mm in thickness. In the coated and thermoset bonded form, a substantially lesser amount of the viscoelastomeric insert 3 may be typically utilized for certain applications to provide the desired cohesiveness and adhesiveness. Typically, an insert 3 in the tightly bonded form or unbounded form will be less than about 60 mil in thickness and most typically fall within a thickness range of about 20 mil to about 50 mil. Thicker sizes may be used, but are generally unnecessary. The insert 3 will be sized to accommodate the container combination 1 and the stowed item 20.

Traditionally polyurethanes are generally formed by reacting a polyol with an isocyanate usually a di- or polyisocyanate, such as aromatic isocyanates (e.g., typically a diphenylmethane diisocyanate (MDI) or tolune diisocyanate (TDI)) and aliphatic isocyanates such as hexamethylene diisocyanate (HDI) or isophorone diisocyanate (IPDI), in a prepolymer form which serves as the polyurethane isocyanate reactant in a reaction media, which may contain an epoxidized vegetable oil as the major reaction media component. The reactant components include the isocyanate prepolymers reacted diols and triols polyoxyakylene polyol prepolymers, such as polyethers having terminal diol and triol groups (e.g., polyoxyethylene and/or polyoxypropylene diols and triols) typically of a molecular weight of more than 1,000.

The triols within the reaction media cause cross-linking at the three available hydroxyl groups, whereas the diols provide an uncrossed-linkage or straight chain linkage within the thermoset polymeric structure. In order to achieve a highly effective stable cohesive and adhesive insert 3, a proper proportional amount of cross-linkage and straight chain linkages is necessary. The thermoset polymeric structure necessitates somewhat of a lessened cross-linked structure, along with a more pronounced presence of intervening straight chain polar attracting linkages, to provide a more flexible viscoelastomeric backbone chain of an appropriate polarity for the hosting of the polarized plasticizers therein. This creates an intertwining backbone chain providing an excellent attractive force and cohesive polar alignment of plasticizing agent throughout the entire viscoelastomeric mass. Exemplary useful triols and diols have repetitive oxygen groups of higher molecular chains, such as polyethers and polyesters containing either polymerizable terminal diol or triol groupings. Since it is desirable to utilize polymerizable reactants which provide a lower workable viscosity for prefabrication of the curing reaction media into the desired manufactured form, the more fluid diols and triols (as well as plasticizers) provide a more easily workable viscosity range. The resultant reaction product of balanced cross-linkage and straight chain polarized linkages, with a balanced plasticizer content homogeneously distributed within the polymeric network, has been accordingly found to unexpectedly exhibit superior adhesiveness and cohesiveness, rendering it particularly useful as an insert 3 herein. The uncured reaction media, when cured, creates a thermoset chain, which when properly loaded with an effective amount of a plasticizer, becomes homogeneously distributed within the thermosetting reaction media to provide the desired cohesive and adhesive characteristics, which renders the thermoset viscoelastomeric reaction product unexpectedly effective for use as an insert 3 herein. The adhesive and cohesive stability of the resultant thermoset reaction product requires a delicate balance between molecular cross-linkage and polar aligning straight chain thermoset moieties bridging structure, including the ratios thereof, as well as the level and type of plasticizer and its content within the thermosetting reaction media. Generally a lowering of the plasticizer content leads to a firmer and less tacky reaction product, while an excessively high diol reactant level can lead to a thermoset reaction product, which upon contacting a stowed item, becomes permanently bonded to the stowed item 20. By an atypical reduced plasticizer content and a judicious control of the diol and triol ratio, a viscoelastomeric thermoset reaction product ideal for use as an insert 3 is possible. The appropriate plasticizer content, in combination with an increased polyether diol concentration within the thermosetting reaction media, increases cohesiveness and tensile strength, as well as thermoset softness. The increase in the proportionate amount of polyether diol to polyether triols, in combination with the plasticizer, provides adhesive stability, which effectively permits the insert 3 to functionally possess a releasability of an item 20 when stowed over prolonged stowing times. The loading of the reaction media with a lower molecular weight polar plasticizer permits a reduction in the total plasticizer content, which in combination with the increased polyether straight chain linkage, provides an insert 3 possessing an unexpected stowing and releasability efficacy when used in the storage container combination 1. The lower molecular weight plasticizers also tend to contribute to a more fluid curing reaction media, which may be more easily fabricated into a cured reaction product of the desired prefabricated form.

When working with vegetable oil based plasticizers, the reaction media desirably includes a measured amount of epoxidized oil component content (e.g., fatty triglycerides such as epoxidized soybean oil (ESO)) amounting to less than 50 percent of the total reaction media weight (but may still constitute a predominant reactant reaction media ingredient), along with an increase in the polymerizate level of the straight chain viscoelastomeric components (e.g., the polyether diols) within the thermosetting media. Surprisingly, by reducing the triglyceride oil (e.g., epoxidized) content and increasing the proportion of the straight chain forming thermoset polymerizable reactants, the cured tackiness of the insert 3 will dramatically increase, even though the reaction media may still contain a triglyceride component (e.g., ESO-epoxidized soybean oil) as a predominant component. Increasing the compositional cohesiveness and adhesiveness generally entails decreased epoxidized oil content, as well as a decrease in the cross-linking triol reactant, leading to a substantially reduced cross-linkage in the polymeric structure, with a concomitant increase in the straight chain producing diol reactant level, which increases the intervening straight chain bridging structure within the thermoset viscoelastomeric molecule. This polymerizate molecular change (with or without the use of other conventional plastic plasticizers, besides the epoxidized triglyceride) apparently creates a localized polymeric polarity charge effectively expressed by the unique oxygen-containing viscoelastomeric polyether backbone structure intertwined within the cured reaction product mass, leading to an effective polarized plasticizer loading, ultimately resulting in outstanding adhesiveness and cohesiveness, coupled with its ideal release properties. Effective cohesive and adhesive efficacy for the insert 3 may be achieved with a triglyceride content ranging from about 15 to less than 50 percent by weight of the total reaction media weight. The substitution or replacement of the epoxidized triglycerides with polar ester plasticizers (especially those of a substantially lower molecular weight) have been found to maintain a desired level of cohesiveness and adhesiveness, while still retaining excellent releasability and stability properties. Certain polar ester plasticizers of a more fluid consistency at room temperatures, and typically of a relatively low molecular weight, will contribute to ideal working viscosities during the initial curing stages, rendering the reaction product and insert 3 prefabrication much easier. Typically, these more fluid ester plasticizers will have a molecular weight of 500 or less.

Illustrative of an insert 3 having an exceptionally high degree of cohesive and adhesive efficacy in the container combinations 1 as depicted in FIGS. 1-4 may be appropriately prepared by selectively using a thermosetting precursor reaction media, which provides a properly configured carbamate thermoset linkage (e.g., urethane) for the thermoset viscoelastomer. In general, the applicable thermosetting polyurethane precursor mixes for preparing the insert 3 will typically include a balanced amount of a polyol prepolymers (e.g., diols and triols) reacted with a ring-opening species of a hardener (e.g., amines, amides, mercaptans, anhydrides, polycyanates such as a diisocyanate, etc.). The ratio of polyol reactants, hardeners, catalyst, reaction temperatures, etc., are pre-selected with an appropriate balance given to the diol and triol reactants to molecularly create the appropriate cross-linkage and linear linkage needed, in combination with selective plasticizers and amounts, to provide the unique stability, cohesiveness and adhesiveness of the thermoset viscoelastomeric reaction product for the insert 3. The use of reactants, catalysts, reaction temperatures, etc. causing an excessively cross-linked thermoset polymers without sufficient straight chain polyether bridging between the cross-linkages are generally unsuitable to create the desired adhesiveness and cohesiveness for the unique viscoelastomer and the insert 3. The thermosetting reactants are thus chosen so as to avoid an undesirably high degree of cross-linkage and a corresponding high glass transition temperature. Reaction conditions and reactants which favor a more linear, cohesive and adhesive viscoelastomeric thermoset backbone structure receptive to polar plasticizer loading are particularly well suited for use in providing the insert 3 herein. Since the more exothermic, elevated curing temperatures are more conducive to creating a more rigid thermoset, the reactants and reaction media selection, slower reaction rate catalysts, low curing temperatures, controlled curing times and triol cross-linking to diol straight chain producing reactants, in combination with an effective plasticizer loading, are precisely controlled in order to impart the desired insert 3 characteristics. Carefully controlled reaction media conditions, coupled with the proper reactants and plasticizers, will accordingly provide a more flexible, lower degree of cross-linkage and a lower glass transition temperature to yield a highly cohesive and adhesive thermoset reaction product. Apparently, the particular thermoset molecular configuration created by a proper balance between the cross-linkage precursors and the straight chain polymerizates configures the thermoset viscoelastomeric polymerizate to a form that is highly susceptible to effective plasticization with the appropriate polar plasticizer orientation being created within the thermoset viscoelastomeric labyrinth polymerizate structure to yield the desired unexpectedly superior cohesive and adhesive properties. The desired thermoset insert 3 will be further characterized as being a viscoelastomeric thermoset polymer exhibiting low rebound velocity and hysteresis properties, in addition to unexpectedly superior cohesiveness and adhesiveness. Such thermoset viscoelastomers also characteristically exhibit excellent energy and attenuating properties capable of withstanding repetitive and prolonged shock stress without structural damage or any substantive sag or rebound loss.

Procedurally, the reaction product preparation may illustratively involve a thermosetting a reaction media homogeneously loaded with plasticizers, which may include an epoxidized vegetable oil reaction media component as a predominant media weight, but not as a major media component (e.g., more than about 15% but less than 50% of the total reaction media weight) as well as other desired plasticizers, a carefully measured molar ratio of cross-linking polyols to straight chain producing polyether diols, to reduce overall cross-linkages to create a desired bridging thereof with straight chain linkages, an isocyanate prepolymer hardener such as aliphatic, aromatic, heterocyclic, etc., polyisocyanates, cycloaliphatic, arylaliphatic, isocyanates, and an appropriate catalyst (e.g., slow acting). The reaction media contains an appropriate plasticizer loading specifically adapted to provides a curable reaction media, which upon curing, produces a viscoelastomeric reaction product having a unique polymerizate structure effectively loaded with polar oriented plasticizers uniformly or homogeneously distributed throughout its entire mass intertwined and supported by the thermoset polymerizate structure. Illustrative catalysts include tertiary amines, tertiary phosphines, strong bases (e.g., alkali and alkaline earth metal hydroxides, alkoxides and phenoxides), and acidic metal salts of strong acids, metal chelates, metal alcholates and phenolates, organic acid salts, organo metallic derivatives, etc. Under the most desirable thermosetting and fabricating conditions, the polymerizate precursors and the plasticizers are provided in the reaction media as room temperature liquids without necessitating any solvents, other chemical dispersion aids or elevated temperatures to homogeneously disperse the reaction media components.

The diols and higher polyols of a relatively high molecular weight will effectively serve as thermoset viscoelastomeric cross-linking and straight chain building components for the intertwining thermoset viscoelastomeric polymeric structure, which when properly balanced, provide a plasticizer friendly viscoelastomeric polymeric structure of a well-balanced straight and cross-linked linkages of an appropriate polymerizate configuration and molecular polarity for plasticizer loading. On a reactant weight percentage basis, the diols are generally recognized as being less effective than the triols in producing shock absorbing polymeric structure, but are extremely effective herein in creating the desired viscoelastomeric polymeric structure necessary for plasticizer loading and imparting the desired unique adhesiveness, cohesiveness and release characteristics to the insert 3. A judicious diol to triol balance enables a balanced proportion of polarized plasticizing components to effectuate the superior adhesiveness and cohesiveness within the carefully structured thermoset reaction product structure. To achieve the necessary plasticizing adhesive and cohesive efficacy, the straight chain diol precursors are typically of a relatively high molecular weight as may be provided by a polyether sequence, which at increased reaction media concentration, creates a more linear thermoset polymeric polyoxy structure, while also serving to lessen the cross-linkage density. In general, the desired plasticity and flexibility, along with the desired polarity, adhesiveness and cohesiveness, may be accordingly effectively effectuated via interpolymerizing the proper amounts of the thermosetting higher molecular weight diols and triols of polyols (e.g., molecular weight 2,000-10,000) along with other thermosetting isocyanate reactants and plasticizers at the appropriate reaction media amounts. The useful polyether diols herein are characteristically comprised of a straight polyether molecular chain having two terminal hydroxyl groups. In contrast, the polyether triols characteristically have three cross-linking reactive hydroxyl groups leading to more polyfunctional cross-linking sites in the thermosetting reaction media.

When using the ether polyols, the basic molecular structure of the thermoset reaction product typically requires a controlled cross-linked structure by balancing the dihydoxy to trihydroxy polyalkylene oxide ratio to create a thermoset viscoelastomer having a sufficient quantum of straight chain polyether linkages. The polar oxygen rich diol reactant serves to separate and becomes sandwiched between the cross-linking triol polymerizate linkages. The effective reduction in cross-linkage does not change its thermoset viscoelastomeric classification since its viscoelastomeric properties are retained. Apparently, the controlled thermoset structure permeating the reaction mass creates a controlled polar density of cross-linked polyethers interspersed amongst straight polyether chain bridges to provide a unique labyrinth structure, which apparently provides an appropriate polarity and allows for an effective loading of the necessary adhesive and cohesive contributing factors, which include the use of plasticizers, such as those commonly known by the trade as plastic plasticizers. By establishing a viscoelastomeric molecular structure loaded with properly oriented and entrained plasticizers, surprisingly superior adhesive and cohesive properties with stable release attributes are thereby achieved. Countless enclaves of negatively charged straight and cross-linked diols and triols appear to form a thermoset labyrinth loaded with polarized plasticizer uniformly distributed throughout the curing reaction media and the cured reaction product. This unique polarized polymerizate infrastructure and massive polarized plasticizer stacking within the polymerizate labyrinth apparently creates a synergistic adhesive and cohesive reaction product effect. The reaction product and the viscoelastomeric inserts 3 possess a surprisingly high tensile strength and softness indicative that its cohesive thermoset viscoelastomeric structure, coupled with its plasticizer content, significantly contributes towards a superior compositional cohesiveness and adhesiveness. Along with its high tensile strength, the reaction product and the viscoelastomeric insert 3 possess a high degree of elasticity.

The epoxidized vegetable oils may effectively serve as a plasticizer in combination with the bridging straight chain polyether diol polymerizate to create the desired cured flexibility, plasticization, releasability, cohesion and adhesion efficacy for the cured viscoelastomeric thermoset insert 3. Particularly effective cohesive and adhesive properties arise when the epoxidized vegetable oil concentration range is less than 50 percent by weight, with an amount less than 45 percent of the total reaction media weight providing further enhanced adhesive, cohesive and stability efficacy.

The lower molecular weight plasticizers (e.g., particularly the less than 500 MW ester plasticizers) may be effectively used to replace the epoxidized vegetable oil plasticizer. Substitution of the epoxy triglycerides with the ester plasticizers of a lower molecular weight will significantly increase fluidity and workability of the thermosetting reactants while still retaining the other desirable thermoset or insert attributes. Plasticizer (particularly the lower weight esters) coupled with a balanced triol and diol ratio can be effectively utilized to provide a reaction product and insert which will tenaciously cure and bond to a supportive base 5. The weight ratio of epoxidized triglyceride to ester plasticizer (if present) may typically range from about 1:3 to about 3:1 and most typically between about 1:1 to about 3:1. The epoxidized vegetable oil (e.g., epoxidized soy bean oil is commonly referred to by the trade as ESO) may typically comprise a predominant weight portion of the total reactant media with amounts ranging from about 20 to less than 30 percent by weight of the total reaction media weight being highly effective for certain applications. The molecular size and configuration, polarity, functional molecular groups, etc. of the thermosetting polymeric reactants, along with the combination of lower molecular weight ester plasticizer and the epoxidized vegetable oil in measured amounts, can be used to effectively contribute towards the creation of a desired insert 3 possessing the desired unique cohesive and adhesive properties. Although the epoxidized vegetable oil may include a variety of epoxidized vegetable oils (e.g., castor, corn, cottonseed, perilla, safflower, linseed, soybean, tall, etc.), epoxidized soybean oils have been found to be particularly effective as the epoxidized vegetable oil component for preparing the reaction product and the thermoset viscoelastomeric inserts 3.

Imparting the desired flexibility, adhesive and cohesive characteristics to an insert 3 compatible for interfacing onto the container confining walls 5W including the container bed 5B and stowed items 20 confined thereby may be illustratively prepared via utilizing a reaction media containing about 15 to about 30 parts by weight of a two functional polyether polyol (e.g., ELASTOCAST C-4057, available from BASF Corp.), about 15 to about 35 parts by weight of a three functional polyether polyol (e.g., ELASTOCAST C-4018 available from BASF Corp.), about 4 to about 10 percent by weight of methylene diphenyl diisocyanate based glycol prepolymer (e.g., ELASTOCAST TQZ-P23 available from BASF Corporation, or sold by Dow Chemical as Isonate 2181° and Rubinate 1790[6]), an epoxidized soybean oil in an amount ranging from about 25 to less than 50 percent by weight of the total reaction media weight, along with a catalytic amount of suitable catalyst (e.g., a Bismuth (3+) neodecanoate, such as COSCAT 83 available from Vertellus Specialties) typically at a catalytic concentration ranging from about 0.1 to about 0.6 percent by weight of the total reactant weight. The polyether diols and triols are available at various chain lengths typically ranging from about 1,000 to about 20,000 molecular weight. The polyether diols and triols most suitably adaptable herein will have a molecular weight of less than 15,000, and most typically less than 10,000. Since there exists definitive advantages in maintaining fluidity during the initial mixing and prefabricating steps, the more fluid polyethers are more useful for most applications. Exemplary of the diol and triol reactants applicable herein include the polyoxyethylene and polyoxypropylene diols and the triols thereof are those having a molecular weight generally ranging from 1,000 to 8,000. Particularly effective for use herein are the polyether diols within about the 2,000 to about 6,000 molecular weight range and triols within about the 2,000 to about 8,000 molecular weight range, and most particularly from about 3,000 to about 5,000 MW. As mentioned, care needs to be exercised as to the extent of cross-linkages and intervening polyoxyalkylene linkages separating the cross-linking sites. This is generally accomplished by retaining the diol to triol weight ratio content from about 7:13 to 13:7, and most typically from about 3:2 to about 2:3, to provide the desired straight chain polyether linkage and cross-linkage density.

As a reaction media component, the epoxidized vegetable oils are compositionally effective in providing adhesiveness, cohesiveness and plasticization for the insert 3. The epoxidized triglycerides of the vegetable oils also uniquely contribute towards the desired prerequisite viscoelastic properties, while further imparting the desired cohesive attributes adaptable for use in combination with the confining container 5 and the items 20 desirably immobilized by the interfacing section 3. As may be observed from the aforementioned formulations, the epoxidized vegetable oil may suitably constitute the predominant ingredient, but at a level of less than 50 percent of the total weight of the uncured reaction media. Initially, the uncured reaction media may most appropriately be formulated so as to possess sufficient flow characteristics to allow the uncured reactants to be pre-formed into a desirable cured shape for use as the insert 3 herein. The total plasticizer content will most typically fall within about 25 to about 45 percent by weight of the total reaction media weight. Superior adhesiveness and cohesiveness will most generally be accomplished by maintaining the total plasticizer content range from about 30 percent to about 40 percent of the reaction media weight.

In general, the cured thermoset viscoelastomeric composition prepared from uncured reactants of a high epoxidized soybean oil content will adhere to adhesively compatible polymeric materials, such as polyurethanes and PET (e.g., polyethylene terephthalate), polyolefins (e.g., polyethylene, polypropylene), polyacrylates, etc., while other halogenated materials such as the halogenated polymers as exemplified by polyvinylchloride (PVC) will not be adhesively compatible (except for special formulations) but none-the-less provide excellent release properties which render such polymers particularly effective for use as a mold to cure the reactants. However, as illustrated by Example 3, reaction medias designed to tenaciously adhere to normally non-adherent plastics upon curing may be prepared by a properly balanced reaction media.

Another observed unique insert feature resides in the manner in which the thermoset reaction product and the insert 3 will adhesively interact with items 20 adhesively attached thereto. This adhesive interaction is generally characterized by a slight initial increase in adhesiveness within about 5 to about 10 seconds after its initial adhesive attachment to an item 20, which is then followed within 60 seconds by a stabilization to 90% of its maximum or ultimate adhesive attraction. This slight change in adhesiveness may be indicative of an intermolecular realignment, coordinate covalent bonding, or polarization of the plasticizing components, or other molecular interaction within the viscoelastomeric reaction product structure to provide for a delayed increase in adhesive attraction.

The preparation of the superior cohesive and adhesive viscoelastomeric thermoset reaction product and its inserts 3 necessitates controlling the cross-linkage at a level sufficient to retain its thermoset viscoelastomeric polymeric structure. Excessive molecular chain cross-linkage caused by the triol and higher polyhydroxyl components, along with the isocyanate thermosetting reactants, results in a viscoelastomeric structure that cannot be effectively loaded with an effective polarized orientation of the plasticizing component, which is functionally essential to impart the superior cohesiveness and adhesiveness to the thermoset viscoelastomeric reaction product. If the viscoelastomeric cross-linkage is reduced too much, the polymeric structure is converted into a non-functional viscoelastomer or non-homogenous thermoplastic mass, which is molecularly and structurally incapable of retaining any cohesive and adhesive imparting components to a sufficient degree to provide a thermoset viscoelastomer possessing a releasable adhesive value of more than 300 $g_f/cm^2$. A properly balanced negatively charged enclave formed by monitored amounts of triol and diol polymerization precursors in the presence of a heavy load of polar orientable plasticizers effectively oriented within the thermosetting reaction media and the thermoset appears to create a desirable synergistic cohesive and adhesive effect to the reaction product. Whether or not the proper viscoelastomeric thermoset polymerizate structure and a sufficient amount of plasticizer have been achieved may be ascertained by determining whether or not an adhesion release strength of more than 300 $g_f/cm^2$ has been achieved. Excessive plasticizer concentration exceeding the thermoset viscoelastomeric loading capacity will typically lead to unbounded plasticizer visible upon the viscoelastomeric reaction product surface. Conversely, an inappropriate diol to triol reaction media ratio will fail to provide the necessary polymerizate structure needed to achieve an adhesion release strength of more than 300 $g_f/cm^2$. Typically, a highly functional adhesive thermoset viscoelastomeric insert 3 will characteristically possess the uniquely distinctive adhesive and cohesive attributes as mentioned herein. By providing the appropriate cross-linkage sites to polyether straight chain linkage with an appropriate plasticizer loading, adhesion release strengths or separation values of more than 400 $g_f/cm^2$, and typically greater than about 500 $g_f/cm^2$ may be effectively achieved.

In essence, the diols and triols useful in preparing the thermoset reaction products of a desired polymerizate structure are derived from oxygen containing hydrocarbyl diols and triols of a molecular weight of at least 1,000 and include repetitive oxygen containing functional groups such as provided by the polyester and polyether grouping. Due to the oxygen electron scavaging effect to satisfy its $2s$ orbital needs, it appears that these repetitive internal oxygen containing groupings sandwiched between cross-linkages provide countless polarized enclaves for uniformly hosting corresponding massive polarized plasticizer concentrations within the polymeric structure to collectively create a synergistic cohesive and adhesive effect thereupon. Although the aforementioned viscoelastomeric reaction media primarily centers about viscoelastomers prepared from a thermosetting reaction media incorporating a balanced cross-linkage triol and diol ratio with the cyano reactant in the presence of a sufficient amount and type of plasticizer to provide the desired adhesive and cohesive insert, it is contemplated that this technology may also apply to other thermoset viscoelastomeric producing reaction products having a properly balanced cross-linked molecular structure separated by a proper amount of straight chain polyoxy linkages and polarity in the presence of sufficient adhesive contributing plasticizer to yield a thermoset viscoelastomeric reaction product insert 3 of a comparable stable cohesiveness, adhesiveness and releasability. In general, the thermosetting viscoelastomeric reaction media is accordingly formulated with the appropriate level of cross-linkage and straight chain reactants containing a sufficient amount of a plasticizer to create the unique highly cohesive and adhesive viscoelastomeric insert 3. As pointed out in the parent application incorporated by reference herein, a viscoelastomeric reaction media favoring a substantially lesser cross-linked viscoelastomer loaded with a lesser amount of epoxidized vegetable oil plasticizer had been found to unexpectedly dramatically increase the adhesiveness and cohesiveness of the reaction product. It has also been discovered that other commonly used plasticizing agents for plastics which are unreactive with the viscoelastomeric reaction media reactants may also be effectively used to impart a high degree of adhesiveness and cohesiveness to the reaction product. Such plasticizing agents in conjunction with the epoxidized vegetable oil plasticizer (especially ESO) may be effectively used to impart enhanced tensile strength and softness while also providing a thermosetting reaction media of an exceptional viscosity and workability in the manufacture of the inserts 3.

The most appropriate adhesive strength for any application will depend to a certain degree upon the particular item 20 to be stored. The cohesiveness and adhesiveness of the thermoset viscoelastomer and insert 3 may be adjusted by plasticizer type and its loading to fit the item 20 to be stowed. Typically, the adhesion release strength may be selectively predetermined prior to the thermosetting reaction product preparation so as to match its intended or desired end use. The adhesion release strength may be regulated by the amount and type of plasticizer used and the polymeric configuration of the thermoset viscoelastomer achieved by the curing of the appropriate reaction media polymerizates. The molecular polymeric structure of the thermoset viscoelastomer may be modified by the cross-linkage density and straight chain linkage present in the thermoset reaction product so as to enable the polymeric structure to house an effective cohesive and adhesive quantum of plasticizer.

The desired adhesion release strength for any insert 3 will depend largely upon the type of container combination 1 and item 20 to be stowed therein. The size, delicacy, configuration and weight of the stowed item 20 will generally establish which releasable adhesive strength value is best suited for any particular end use or stowed item 20. Fragile items 20, such as Christmas tree decorations, glass, and medication will normally require a lesser degree of adhesiveness (e.g., 300-400 g./cm$^2$) which will allow for a less forceful release of the fragile item 20 without damage. Similarly, a heavy hammer 20 may not be adhesively matched by an excessively adhesive insert 3 if the force required to separate the hammer 20 from the insert 3 would make it manually very difficult to separate the hammer 20 from the container 5 or the insert 3. This excessive adhesiveness may cause the container 5, as well as the adhesively stowed hammer 20, to be lifted together without any hammer 20 separation from the insert 5. However for certain applications, an insert 5 having a high degree of adhesive strength may be particularly desirable. For example, certain toss games or other grounded devices necessitating a firm grounding of the gaming device would allow for the use of an extremely high adhesive release strength (e.g., 1,200-1, 600 g./cm$^2$). Since the thermoset viscoelastomeric reaction product characteristically possesses an extremely high internal cohesiveness which prevents its internal separation, the thermoset viscoelastomers are uniquely useful for diverse needs requiring a releasable, high tensile strength adhesive which fully retains its structural integrity upon release.

As evident from the aforementioned, the most suitable adhesive strength for the inserts 3 and the thermoset viscoelastomeric reaction product ultimately depends upon its intended end usage. The adhesive strength, the cohesiveness, the thermoset reaction media attributes, the compositional uniformity, the releasability, antimicrobial, and a host of other factors, are attributes which uniquely distinguish the inserts 3 and the cured thermoset viscoelastomeric reaction product from all other adhesives. For most applications, an insert 3 and the cured thermoset viscoelastomeric reaction product will normally have an adhesive release strength ranging from more than 300 g./cm$^2$ to about 1,200 g./cm$^2$, and most typically within the range of about 500 g./cm$^2$ to about 1,000 g./cm$^2$. As previously mentioned, substantially higher adhesive strengths may be achieved, but may have a more limited utility.

By providing the proper thermosetting polymerizable precursors in the appropriate amounts, the basic thermoset viscoelastomeric chain provides a basic molecular structure especially adaptable for in situ loading with plasticizer, which depending upon type, can be used to beneficially to alter the adhesive and cohesive characteristics of the cured viscoelastomer. An effective amount of long chain polyether polymeric linkages, coupled with the appropriate isocyanate and triol cross-linkages, provide a polymeric chain of a desired polarity having an unexpectedly high affinity for a loading of polar plasticizing components within the thermoset viscoelastomeric reaction product infrastructure. The selection of the particular plasticizing agent and its concentration can have a pronounced effect upon the adhesiveness and cohesiveness of the thermoset viscoelastomeric reaction product. This may be exemplified by the loading of the viscoelastomeric reaction product with ester plasticizing agents, which are typically made by reacting an alcohol with a fatty acid. The ester plasticizers include the ester condensation product of an alcohol ($C_1$-$C_{18}$) with polycarboxylic acids, which esters can be used to an advantage in preparing a thermosetting reaction media and thermoset viscoelastomeric reaction product having an adhesiveness tailor-made for a particular end use. For example, certain applications will require a tenacious adhesiveness whereas other applications are best matched with a milder releasable adhesive characteristics, such as for fragile items 20. Similarly, the type of plasticizer (e.g., dibutyl sebacate) may be used to advantage in preparing an uncured reaction media having an exceptional low initial viscosity rendering the uncured reaction media especially suitable for reaction product prefabrication. The polar strength (often referenced as "dipole moment") of these plasticizing esters depends to certain degree upon the alcohol condensation reactant chain length which also has an effect upon the adhesive characteristic of the thermoset viscoelastomeric reaction product.

Although the thermoset viscoelastomeric structure is especially adapted to loading with a host of plasticizers, plasticizers having a polar attraction to the viscoelastomeric polymeric structure are particularly applicable. This molecular electronic attraction apparently contributes to the unique adhesive and cohesive properties within the reaction product. Since the plasticizers are not effectively loadable into a cured thermoset viscoelastomer, the plasticizing reagents are necessarily uniformly incorporated into the thermosetting viscoelastomeric reaction media to achieve the desired uniform and homogeneous distribution thereof throughout its entire uncured composition. The thermosetting conditions apparently uniformly align the polymerizate reactants with an effective synergistic polar positioning and alignment of the polar attracting molecular chain sections of the thermoset reactants with the plasticizer to provide for a highly effective polarized plasticizer loading and alignment therewithin. This permits a tenacious and cohesive loading of plasticizer without any evidence of plasticizer seepage or separation from its hosting thermoset viscoelastomeric polymeric structure.

In general, plasticizers which are suitable as plasticizing agents for polyvinyl chlorides are generally applicable for use as reaction media plasticizers herein. Plasticizers of a higher dipole moment (e.g., dibutyl sebacate (DBS) having a dipole moment of 2.48 debyes (D)) will tend to impart certain desired properties to the polymerizate. Illustrative of plasticizing agents which may be combined with the thermosetting reaction media include the ester plasticizers such as sebacates, adipates, terephthalates, dibenzoates, glutarates, phthalates, azelates, etc. of the $C_1$-$C_{18}$ chain ester type adhesiveness. However different blends of the ester plasticizers may be co-blended into the thermosetting reaction media to create or modify the effective working viscosity as in the curing or cured form. For unexpectedly superior adhesiveness, cohesiveness and workability plasticizers of a dipolar moment of more than 1.5 D, and typically more than 2.0 D, may be utilized for this purpose. Epoxidized triglycerides, such as the epoxidized animal and vegetable oils, are especially effective as a plasticizer component in the thermosetting viscoelastomeric reaction media, and especially at levels typically less than 40% of the total reaction media weight, with significantly overall improvements being generally accomplished when the epoxidized triglyceride content is less than 35%, and more appropriately less than 30% by weight of the total thermosetting media weight. The incorporation of a lower molecular weight ester plasticizer (e.g., less than 400 MW) (such as an polyalkylene ester plasticizer) in combination with epoxidized triglyceride plasticizer can be utilized to provide an easier fabricating form of the reaction media without adversely affecting its desirable thermoset properties.

Illustrative ester plasticizing agents of a high dipole moment include the dibutyl, dimethyl, diethyl, and dibutyl esters of sebacates, adipates, isophthalates, phthalates, maleates, azelates, glutarates, etc. The total plasticizer concentration will most suitably range from about 20% to about 45% by weight, and most typically range from about 25 to about 40% by weight, with the weight ratio of epoxidized triglyceride to non-epoxidized plasticizer typically ranging from about 1:0 to about 1:3, and most typically from about 1:1 to about 3:1.

The term "cohesive" and "adhesive" herein refer to their common technological meaning. The term "cohesive" and "cohesiveness" refers to the thermoset viscoelastomer cohesive ability to retain its structural integrity when subjected to separating forces. The reaction product and insert cohesive attributes are further reflected by its tensile strength, adhesive separation without leaving any viscoelastomer residue, and its elasticity. In contrast, the word "adhesive" refers to the bonding strength of the thermoset viscoelastomer to items 20 adhering to its adhesive surface. The thermoset viscoelastomeric reaction product and the inserts 3 possess an unexpectedly superior stabilization and a powerful adhesiveness, which is releasable by a counteracting force overcoming its adhesiveness.

As typical with most thermosetting resins, it cannot be precisely ascertained what phenomena actually occurs when an uncured viscoelastomeric reaction media is cured and rigidly bound to a compatible substrate. Whether the thermosetting creates a chemical bonding or an extremely strong molecular or mechanical bonding is unclear. Nonetheless it has been discovered that an increase in the diol to triol weight ratio, coupled with a reduced plasticizer content, will result in a highly tenacious cured bonding of the viscoelastomeric reaction product to a compatible substrate, as well as those substrates recognized as being resistant to bonding. In certain applications, a peelable or more readily releasable cured coating would be desired, whereas in others, a more tenacious bonding is better suited for its end use. Although the curing of the reaction media with the reduced cross-linking triols and plasticizer content affects its supportive base 5 bonding characteristics, the opposing cured surface area (i.e., unbounded surface) still retains all of its desired cohesive and adhesive characteristics for insert 3 usage. The reduced triol and plasticizer content also increases tensile strength, while providing a more permanent bonding to the supportive structure upon which it was cured.

EXAMPLES

Example 1

A thermoset viscoelastomeric reaction product adapted to provide a thermoset viscoelastomeric insert 3 having exceptional adhesive, cohesive and releasability efficacy was prepared by uniformly admixing together a two part thermosetting reaction media mix comprised of:

|  | Percent by Weight: |
|---|---|
| A- Mix: Ingredients | |
| Methylene diphenyl diisocyanate based glycol prepolymer (ElastoCAST TQZP23 by BASF Corporation) | 6.42% |
| Epoxidized soybean oil | 26.9% |
| Dibutyl sebecate | 8.97% |
| B- Mix: Ingredients | |
| Polyurethane precursor mix formulated polyether diol (ElastoCAST C-4057 by BASF Corporation) | 28.53% |
| Polyether triol (ElastoCAST C-4018 by BASF Corporation) | 27.72% |
| Epoxidized soybean oil | 0.00% |
| Catalyst (COSCAT 83) | 0.16% |
| Tinuvin B75 (UV inhibitor) | 1.30% |
| Total | 100% |

Time Sensitivity Test

The uncured admixture was then spread evenly at a uniform 4 mm thickness upon a polyvinylchloride apron and allowed to cure to the desired thermoset viscoelastomeric reaction product. It was observed that the resultant cured reaction product film was removable from the PVC. The reaction product film was then cut into test panel patch sizes for testing using the testing apparatus depicted in FIG. 5 with the testing procedure being conducted in accordance with the testing procedure as set forth in appendix A.

Test samples S prepared from the thermoset viscoelastomeric reaction product formulation of this example consistently provided stabilized test sample results requiring a separation force (i.e., adhesion release strength) of more than 300 g/cm² to separate from the tested samples S from the test probe TP using the test procedure set forth in Appendix A. The effect of time after a test sample initial adhesion to the testing probe TP at the designated time intervals is set forth in the following Table 1.

TABLE 1

Time Sensitive Control

| Contact Time (sec) | Removal Force (gf) |
|---|---|
| 5 | 557 gf/cm$^2$ |
| 10 | 545 gf/cm$^2$ |
| 15 | 534 gf/cm$^2$ |
| 30 | 523 gf/cm$^2$ |
| 60 | 591 gf/cm$^2$ |
| 300 | 545 gf/cm$^2$ |
| 600 | 557 gf/cm$^2$ |
| 900 | 580 gf/cm$^2$ |

It has been consistently observed that other test samples of a 300 g/cm$^2$ plus adhesion release strength will typically also reach more than 90% of their maximum adhesive release strength within one minute after their initial contact with the test probe TP.

Unlike many adhesives which undesirably undergo substantial increases in adhesiveness over prolonged stowing intervals rendering them generally unfit for use as a releasable adhesive, the Example 1 reaction product exhibited excellent stability over extended time periods. After a 6 week test period, the Example 1 reaction product exhibited less than a 10% change in adhesion release strength relative to the adhesion release strength tests taken 60 seconds after the initial test probe TP contact. As evident from the aforementioned, the tested reaction product (as well as in the other reaction products disclosed herein) characteristically exhibited excellent adhesion and cohesion stability, rendering it well suited for use as an adhesive insert 3 for the container combinations 1 herein. Comparatively, it was observed that the dibutyl sebacate plasticizer containing reaction media of this Example 1 substantially reduced the initial uncured viscosity, whereas the 45.84 percent by weight epoxidized soybean oil formulation of Example 2 was more viscous. The more fluid thermosetting reaction media rendered the dibutyl sebacate containing reaction media better suited for many fabrication techniques commonly used to convert the reaction media and the resultant reaction product into a fabricated commercial product. Uniform dispersal of the plasticizer within the unique thermoset polymerizate structure places constraints upon the use of diluting solvent based systems, while the application of higher temperatures prematurely hasten curing. Similarly, the polyether and polyester diols and triols of an excessive molecular weight are typically a solid or are waxy, which limits their effective prefabrication usage.

Effect of Pressure

In order to test the effect of an initial application of pressure and essentially a nominal pressure application by the testing probe TP upon test samples S, an applied force of a 110 grams of weight and essentially a nominal application force of comparative tests were conducted in order to ascertain the effect pressure had upon adhesion. The test samples S were secured to the movable test platform after which a uniform pressure of 110 g/cm$^2$ was applied to the probe TP to test the pressurized test samples S. Similar comparative tests were conducted using the same test apparatus and procedure, except that only a nominal pressure (relying solely upon free hanging probe TP of 20 grams) was applied to the test samples S. The testing apparatus D with the test samples S secured to the test platform PF were then subjected to a constant speed withdrawing force using the testing apparatus D shown in FIG. 5. The counteracting force needed to break or separate the adhesive bond (i.e., adhesion release strength) between each of the test samples S and the probe TP was then determined.

It was observed that the application the 110 grams of pressure by the testing probe TP upon the tested samples S initially resulted in a quicker and higher adhesion release strength (e.g., within 15 seconds) than the adhesive release strength of the nominal applied pressure tests which took a substantially longer period of time to obtain their maximum adhesive release strength. However, the nominal applied pressure test probe TP tests ultimately achieved an adhesion release strength comparable to the pressure applied testing probe sample tests. Obviously, the adhesive forces in the nominal pressure applied test probe TP caused the viscoelastomeric reaction product test sample S to internally undergo further adhesive attractive forces without any other extrinsic factor being attributable to its increase in adhesiveness. This subsequent increase in adhesiveness after initial testing probe TP contact for the nominal pressurized test probe TP application tends to indicate that an internal polarity change within the tested reaction product after initial probe TP contact may have occurred, which phenomenon may be due electron migration within the thermoset viscoelastomeric mass after the initial probe TP contact to the sample S. This delayed adhesive attraction may also possibly arise by reason that the sample S draws the test probe TP deeper into the sample S creating a greater adhesiveness, or some other unknown phenomenon may exist.

Thermosetting Bonding Characteristics

An uncured admixture of this example was then spread evenly at a uniform 3 mm thickness upon a polyvinylchloride film and allowed to cure to the desired thermoset viscoelastomeric reaction product, which after separation from the PVC film, was then cut into insert test panel patch sizes for testing using the testing apparatus depicted in FIG. 5. The resultant cured reaction product coating exhibited an increased bonding strength between the cured reaction product and the PVC film. The PVC film could nonetheless be manually separated from the reaction product film. By peeling the cured reaction product from the PVC film, the entire PVC film could accordingly be removed from the thermoset viscoelastomeric reaction product film. By covering both surfaces of the thermoset reaction product with protective plastic films (e.g., PVC films) or other plastics to sandwich the reaction product therebetween, a ready-to-use and protected insertable insert 3 requiring only a stripping of the overlaying protective films from the reaction product insert 3 and its ultimate insertion to the container 5 may be effectively provided for consumer use. The reduced plasticizer level to less than 40% by weight of the reaction media weight tends to enhance the bonding attributes of the cured reaction product coating. The outwardly and unbound surface of the reaction product test sample however possessed excellent stowing attributes. This example illustrates the versatility in preparing reaction products and inserts 3 which permanently bond to a diverse range of base supports 5, including those which do not normally bond to a urethane thermosets.

Permanent Coating Bonding

A freshly uncured reaction media of this example was used to coat a high density polypropylene supportive base 3 mm coating to a pre-flamed bed 5B of a polypropylene fishing tackle box 5. The reaction media was allowed to cure and bond to the bed 5B. The cured reaction product insert 3 had virtually all of the characteristics of a chemically or permanently bonded coating, which could not be effectively removed from the polypropylene container bed 5B. However, the opposite unbound reaction product surface retained its excellent stabilized adhesion separation strength rendering it particularly useful as a permanent insert 3 for the stowable container combination 1. This reaction media is especially useful to permanently bond an insert 3 to a host of common thermoplastic.

Plasticizer Variations

Using the basic formulation of this Example 1, the weight amount of the plasticizer was held constant, but the weight ratio of epoxidized soybean oil (ESO) to dibutyl sebacate (DBS) was changed to 1:0 (i.e., all ESO), 1:1 (i.e., 50% ESO and 50% DBS) and 1:3 (i.e., 25% ESO and 75% DBS). The 1-ESO to 0-DBS, the 1-ESO to 1-DBS and the 1-ESO to 3-DBS weight ratios, upon adhesive release strength testing respectively provided values of 568 $g_f/cm^2$, 420 $g_f/cm^2$ and 341 $g_f/cm^2$. It may accordingly be observed that by altering the ratios and type of plasticizer, the adhesive character, the adhesive use and the fabricating properties may be preselected to fit any desired particular end use and purpose.

Example 2

A viscoelastomeric reaction product containing 45.84 percent by weight epoxidized soybean oil plasticizer was prepared by uniformily admixing together a two part thermosetting reaction media mix comprised of

|  | Percent by Weight: |
|---|---|
| A- Mix: Ingredients | |
| Methylene diphenyl diisocyanate based glycol prepolymer (ElastoCAST TQZP23 by BASF Corporation) | 5.56% |
| Epoxidized soybean oil | 44.44% |
| B- Mix: Ingredients | |
| Polyurethane precursor mix formulated polyether triol (ElastoCAST C-4018 by BASF Corporation) | 28.0% |
| Polyether diol (ElastoCAST C-4057 by BASF Corporation) | 17.52% |
| Epoxidized soybean oil | 1.40% |
| Catalyst (COSCAT 83) | 0.52% |
| Tinuvin B75 (UV inhibitor) | 1.12% |
| Colorant | 1.40% |
| Total | 100% |

Thermosetting Bonding Characteristics

The reaction product was prepared by applying a 3 mm thick coating of the reaction media admixture upon a 0.3 mm PVC film and a 0.3 mm high density polypropylene film and cured. It was readily apparent that the cured reaction product coatings were more loosely bound to the PVC film since the film was easily peelable from the reaction product coatings than the Example 1 coating. The adhesive release strength, when cured in situ with the films, was somewhat greater than the maximum adhesive release strength of 490 $g_f/cm^2$ recorded by the test samples of the uncured reaction product.

The reduced plasticizer content, along with a balanced diol to triol ratio, appears to significantly contribute to the bonding strength of the cured reaction media to a host of supportive structures when cured in situ for certain applications a boned but readily peelable in situ cured reaction media coating and protective film covering both surfaces of the cured reaction product insert 3 may be commercially desirable. This provides an insert 3 which may be transported in the channels of commerce and installed in the stowing container combination by the ultimate consumer.

The in situ cured inserts 3 protected on both surfaces by the protective film may be most suitably formulated with about a 40 percent by weight to less than 50 percent by weight plasticizer. At plasticizer levels below the 40 percent level, the peelablility factor becomes more difficult.

Appendix A

The testing apparatus shown in FIG. 5 was used for the adhesive and cohesive testing of various different reaction products useful as inserts 3 herein. With particular reference to the schematic testing apparatus D depiction of FIG. 5 the cohesiveness and adhesiveness of the thermoset viscoelastomeric inserts 3 were tested. The test apparatus D included a motor driven actuator TA taken from a standard remote controlled electric garage door opener. The actuator TA included a reversible constant speed motor (2.7 cm/sec which is occluded from view) serving to drive a remotely controlled reciprocating test probe TP connected to measuring scale MS to measure the amount of applied force (in grams) needed to separate an insert test sample 3 from a circular polished nickel probe TP having a 1.76 $cm^2$ probe surface area. The testing platform TS provides a solid flat level surface of a laterally movable platform PF form which allows for repositioning to provide an accurate repetition of the test results for each tested sample 3. The testing platform TS may thus be repositioned to provide a repetition of an untested section of the insert 3 for further testing. The testing procedure also provides useful in determining the cohesiveness of the insert 3 by noting the presence or absence of insert 3 residue upon the separation of the test probe TP from the sample 3. By measuring the adhesiveness of the test sample 3 under differently applied sample application pressures, the adhesive effect by applying different adhesive pressures and the cohesiveness of the test sample may be determined. Similarly adhesion separation difference or changes measured over timed sequenced intervals may also be determined so to provide adhesive data upon the insert 3 adhesion stability. The test procedure can also be used to provide adhesion data upon short interval adhesion increases following an initial adhesive attachment of the probe TP to the test sample. Difference in adhesiveness between pressure and non-pressure applied test probe over timed intervals may also be determined.

With reference to FIG. 5, the following methodology was used to test adhesiveness and cohesiveness of various tacky materials:

1. Scope
   1.1. This method measures the level of tackiness exhibited by adhesive materials taking into account time dependent adhesive properties.
   1.2. This test is designed for use with materials that exhibit adhesive properties but may not explicitly classed as adhesives. The test applies to traditional time sensitive adhesives.
   1.3. Units—The tested values are based upon grams-force ($g_f/cm^2$) of the force needed to separate the test probe TP from the test sample.
2. Terminology
   2.1. adhesive-like: adj—Having a sticky quality akin to an adhesive, but derives its sticky quality from molecular structure that forms a molecular attraction (rather than chemical bonded properties) which is releasable from adhered objects without leaving behind residue (e.g., cohesiveness). The test is re-applicable to a test sample or insert 3 which may be washed with a mild detergent and water to restore its stickiness when dirty.
   2.2. tackiness: adj—The quality of feeling sticky to the touch.

2.3. time dependent adhesive: n—Has reference to a material whose adhesive strength increases according to duration of the contact time with a contacting surface which characteristic is distinctive from pressure sensitive adhesives since no substantial pressure is required to achieve the increased adhesive strength after initial contact.

3. Summary of Test Method Using the Testing Apparatus Depicted in FIG. 5
   3.1. A sample S of material to be tested is secured (generally by an insert 5 self-adhesive properties) to the testing platform TB.
   3.2. The testing probe TP of apparatus TA is lowered onto the sample S.
   3.3. The apparatus TA remains in contact with the sample S for a designated time period. 3.4. The apparatus TA is raised from the sample S at a constant speed of 2.7 cm/sec measuring the force in grams required to separate the testing probe TP from the sample S.
   3.5. The measured separating force is recorded in $g_f/cm^2$.
   3.6. Steps 3.1—Step 3.5 is repeated so as to obtain a total of 5 tested samples, which are then averaged to yield a final result.
   3.7. Steps 3.1—Step 3.6 is repeated over designated contact time intervals so as to record the time dependent properties of the tested sample S.

4. Significance and Use
   4.1. The testing method is designed to determine the tackiness (releasable adhesiveness) levels of different products and/or formulas. The test provides a measurement for the time dependent adhesive properties of the tested material S.
   4.2. This testing procedure quantifies the strength of tackiness of a time dependent adhesive and cohesive like material.
   4.3. The test results provide data as to the strength of tackiness or adhesiveness as a function of time.

5. Apparatus
   5.1. The testing apparatus TA is illustrated by the schematic depiction of FIG. 5. Alternative materials and configurations to those stipulated may be used as long as they achieve comparable performance and meet the performance stipulations outlined in 5.2. Key elements of the apparatus include:
      5.1.1. A reciprocating mobile actuator MA (e.g., see FIG. 5-A) is responsible for lowering and raising the test probe TP onto the material sample S (FIG. 5-D) at a constant speed of 2.7 cm/sec.
      5.1.2. The scale MS measures the amount of force in grams per square centimeter required to separate the test probe TP from the test sample S.
      5.1.3. The test probe TP is the sole contacting surface with the tested sample S. The contact surface of the test probe TP is a circular nickel polished probe having a total contact surface area of 1.76 $cm^2$.
      5.1.4. The testing platform TB provides a solid, level surface for accurate test results and secures the tacky test material sample S for testing. This platform TB is laterally movable so as to allow for repositioning of the sample S for multiple testing.
   5.2. Regardless of the specific components used, the mobile actuator MA.
      5.2.1. Raises and lowers the probe TP at a constant speed of 2.70 cm/second.
      5.2.2. The accuracy of testing apparatus and test measures force in grams with an accuracy resolution of 5 percent or better.
      5.2.3. Except for pressure applied tests, a constant pressure of 20.0 g for the duration of the test was applied by the free-hanging, weighted probe TP.
   5.3. The test procedure was conducted at ambient temperatures of 18° C. to 24° C. and most commonly at 21° C.

6. Calibration
   6.1. Prior to first use and at subsequent reasonable testing intervals afterwards, the speed rate of the actuator MA is monitored to ensure consistency within the standard outlined in 5.2.1.
   6.2. Prior to first use, the accuracy of the scale MS should be verified against a known weight and adjusted or zeroed accordingly.

7. Procedure
   7.1. Assemble the apparatus TA.
   7.2. Secure a sample S of material to be tested to the testing platform TB, ensuring that the platform TB (20 gram weight of the TB) does not lift free during testing.
   7.3. Lower the testing probe TP onto the test material S, ensuring even contact between the probe TP surface and the tested material S and that the testing scale MS is neither pulling nor applying pressure to the probe TP.
   7.4. Allow the probe TP to remain in contact with the material sample S for the duration of the test period.
   7.5. Commencing the test by raising the probe TP from the test material S.
   7.6. Record the amount of gram-force as measured by the scale MS needed to separate the probe TP from the test material S.
   7.7. Reset the scale MS.
   7.8. Reposition the testing platform TB so that a fresh area of the sample S is tested by the apparatus TA.
   7.9. Clean the probe TP after each testing with a lint free cloth.
   7.10. Repeat steps 7.2-7.9 to obtain a total of 5 measurements.
   7.11. Repeat steps 7.2-7.10 for each duration of testing (at timed intervals 15 seconds, 30 seconds, 5 minutes, 10 minutes and 15 minutes).

8. Calculation and Interpretation of Results
   8.1. Take each of the 5 measurements for a given time duration and calculate the five test sample measurement average to established as a final value. The average tested value is given in the amount of gram-force ($g_f$) representing the required force to separate the probe TP from the material sample S which serves as a measurement of sample tackiness.
   8.2. Repeat 8.1 for all durations tested.

What is claimed is:

1. A stable, adhesive and cohesive thermoset viscoelastomeric reaction product prepared by thermosetting a reaction media comprised of a substantially uniform admixture of from about 4 to about 8 percent by weight of an isocyanate prepolymer, from about 20 to about 55 percent by weight of a plasticizer containing less than 50 percent by weight of an epoxidized triglyceride plasticizer by weight of the reaction media and polyols consisting essentially of straight chain linking diols and cross-linking triols each having repetitive ether groups, wherein the reaction media further comprises a diols to triols weight ratio ranging from about 7:13 to about 13:7.

2. The thermoset viscoelastomeric reaction product according to claim 1 wherein the polyols comprise polyethers having a molecular weight in excess of 1000.

3. The thermoset viscoelastomeric reaction product according to claim 2 wherein the reaction media comprises:

a) a cross-linked thermoset polymerizate obtained by reacting:
  a) from about 4 to about 8 percent by weight of a diisocyanate prepolymer;
  b) from about 25 to about 35 percent by weight of a polyether triol as the cross-linking triols; and
  c) from about 10 to about 35 percent by weight of a polyether diol as the straight chain linking diols; and
b) from about 20 to about 55 percent by weight of the plasticizer uniformly dispersed throughout the reaction media with said plasticizer comprising:
  a) from 20 to about 45 percent by weight of the epoxidized triglyceride plasticizer; and
  b) from 0 to about 40 percent by weight of an ester plasticizer;
wherein the reaction media further comprises a polyether diol to polyether triol weight ratio of about 3:2 to about 2:3; and
wherein the plasticizer is present within the reaction media in an amount sufficient to provide a reaction product possessing sufficient adhesiveness to immobilize an adhesively adhered item against displacement while retaining structural cohesiveness after the adhesively adhered item is separated therefrom.

4. The thermoset viscoelastomeric reaction product according to claim 3 wherein a plasticizer weight ratio of the epoxidized triglyceride plasticizer to the ester plasticizer ranges from about 3:1 to about 1:3 and wherein the ester plasticizer has a molecular weight of less than 750.

5. The thermoset viscoelastomeric reaction product according to claim 3 wherein the reaction media comprises from about 2 to about 20 percent by weight ester plasticizer.

6. The thermoset viscoelastomeric reaction product according to claim 3 wherein the weight ratio of the polyether diol to the polyether triol and the amount of epoxidized triglyceride plasticizer and ester plasticizer provide sufficient adhesion to stabilize the adhesively adhered item against displacement while also retaining sufficient cohesiveness so as to retain structural integrity after adhesive separation of the adhesively adhered item therefrom.

7. The thermoset viscoelastomeric reaction product according to claim 3 wherein the polyether diol and the polyether triol consist essentially of a polyoxyalkylene grouping selected from the group consisting of polyoxyethylene and polyoxypropylene, and wherein each has a molecular weight ranging from about 2000 to about 10,000.

8. The thermoset viscoelastomeric reaction product according to claim 7 wherein the reaction product comprises a sheet or a film having a thickness of less than 200 mil.

9. The thermoset viscoelastomeric reaction product according to claim 7 wherein the plasticizer ranges from about 25 to about 45 percent by weight and the epoxidized triglyceride plasticizer comprises an epoxidized vegetable oil.

10. The thermoset viscoelastomeric reaction product according to claim 9 wherein the ester plasticizer is selected from the ester group consisting of sebacate, adipate, glutarate, dibenzoate, bisphthalate, terephthalate and azelate in an amount ranging from about 2 to about 20 percent by weight of the reaction media weight.

11. The thermoset viscoelastomeric reaction product according to claim 10 wherein the ester plasticizer has a dipole moment of at least 1.5D and a molecular weight of less than 500.

12. The thermoset viscoelastomeric reaction product according to claim 10 wherein the ester plasticizer comprises dibutyl sebacate.

13. The thermoset viscoelastomeric reaction product according to claim 1 wherein the reaction media comprises:
  a) about 10 to about 20 percent by weight of a polyether diol having a molecular weight ranging from about 2000 to about 6000;
  b) about 25 to about 35 percent by weight of a polyether triol having a molecular weight ranging from about 3000 to about 7000;
  c) about 4 to about 7 percent by weight of diisocyanate prepolymer;
  d) about 25 to about 45 percent by weight of an epoxidized vegetable oil plasticizer; and
  e) an ester plasticizer of a molecular weight less than 750 at a weight ratio of the epoxidized vegetable oil to the ester plasticizer ranging from about 3:1 to about 1:3;
wherein the reaction media has been catalyzed in the presence of a catalytic amount of a thermosetting catalyst for curing the reaction media.

14. A stowing container combination for adhesively retaining and cohesively releasing a stowable item stowed at a stabilized stowable position, said container combination comprising:
  a) a supportive base of a sufficient size and structural integrity to support a desired stowable item, and
  b) an insert of a thermoset viscoelastomeric reaction product possessing releasable, cohesive and adhesive properties bonded to the supportive base and compositionally possessing sufficient adhesiveness and cohesiveness to retain a desired stowable item at the stabilized stowable position and to release the stowed item by an applied force sufficient to overcome an adhesive attraction of the item to the insert while leaving no more than a nominal trace of the reaction product upon a released stowed item with the insert being either chemically bonded to the supportive base by a thermosetting bonding of the reaction product to the supportive base or by an adhesive bonding of the insert to the supportive base.

15. The stowing container combination according to claim 14 wherein the insert of the reaction product is prepared by thermosetting a reaction media comprising a substantially uniform admixture of an isocyanate prepolymer, an effective amount of a plasticizer cohesively bound within the reaction product in an amount ranging from about 20 to about 55 percent by weight of the reaction media weight with the plasticizer comprising less than 50 percent by weight of the reaction media weight of an epoxidized triglyceride plasticizer and from 0 to about 40 percent by weight of the reaction media weight of an ester plasticizer, and from about 35 to about 55 percent by weight polyols with said polyols consisting essentially of straight chain linking diols and cross-linking triols each having repetitive ether groupings, and wherein the reaction media further comprises a diol to triol weight ratio ranging from about 7:13 to about 13:7.

16. The stowing container combination according to claim 15 wherein the supportive base comprises a container equipped with a container bed having multiple sidewalls dividing the container bed into multiple compartmentalized sections.

17. The stowing container combination according to claim 15 wherein the insert comprises a reaction product of the reaction media comprising:
  a) a cross-linked thermoset structure obtained by reacting:
    a) from about 4 to about 7 percent by weight of a diisocyanate prepolymer;

b) from about 25 to about 35 percent by weight of a polyether triol; and
c) from about 10 to about 35 percent by weight of a polyether diol; and
b) from about 20 to about 55 percent by weight of a plasticizer uniformly dispersed throughout the reaction product with said plasticizer being comprised of:
a) from about 20 to about 45 percent by weight of the reaction media of the epoxidized triglyceride plasticizer; and
b) from 0 to about 20 percent by weight of the reaction media of the ester plasticizer;
wherein the reaction media further comprises a polyether diol to polyether triol weight ratio of about 7:13 to about 13:7; and
wherein the plasticizer is characterized as being cohesively bound within the reaction product so as to maintain structural integrity of the reaction product upon adhesive separation of the stowed item.

18. The stowing container combination according to claim 16 wherein one or more of the sections are fitted with a removable insert of the reaction product adhesively affixed to the container.

19. The stowing container combination according to claim 15 wherein the insert is bonded by in situ curing of the reaction media to the container.

20. The stowing container combination according to claim 15 wherein the supportive base comprises a flexible support with the insert being adhesively bonded thereto.

21. The stowing container combination according to claim 19 wherein the insert is bonded by curing the reaction media in situ to a flexible supportive base.

22. The stowing container combination according to claim 15 wherein the epoxidized triglyceride plasticizer comprises an epoxidized vegetable oil and the ester plasticizer comprises a dialkyl ester plasticizer having a molecular weight less than 500 in an amount ranging from about 2 to about 20 percent by weight of the reaction media.

23. The stowing container combination according to claim 15 wherein the supportive base comprises a substantially flat supportive base without any other substantial confining structure.

24. The stowing container combination according to claim 15 wherein the insert imparts antimicrobial properties to the stowing container combination.

25. The stowing container combination according to claim 15 wherein the straight chain linking diols and the cross-linking triols comprise either a polyoxyethylene polyol or a polyoxypropylene polyol each having a molecular weight ranging from about 2000 to about 10,000.

26. A storage container combination equipped with a viscoelastomeric thermoset reaction product possessing stable cohesive release and adhesive properties so as to adhesively engage a stowable item at a desired set position and to release the stowable item upon disengagement from the set position while leaving no more than a trace amount of residue of the reaction product upon the stowed item released therefrom, wherein said combination comprises:
a) a supportive base having a sufficient supportive structure to support the stowable item, and
b) a container insert supported by the supportive base wherein said insert consists essentially of the thermoset reaction product, wherein the thermoset reaction product has been derived from a thermosetting reaction media comprising from about 10 to about 35 percent by weight polyether diol, about 25 to about 35 percent by weight polyether triol, about 4 to about 7 percent by weight of a diisocyanate prepolymer, about 20 to less than 50 percent by weight of an epoxidized vegetable oil plasticizer and from 0 to about 40 percent by weight of an ester plasticizer;
wherein the reaction media further comprises a polyether diol to polyether triol weight ratio ranging from about 7:13 to about 13:7; and
wherein the reaction media has been catalyzed in the presence of a catalytic amount of a curing catalyst.

27. The storage container combination according to claim 26 wherein the epoxidized vegetable oil plasticizer comprises an epoxidized soybean oil in an amount ranging from about 42 to about 48 percent by weight of the reaction media, and wherein the polyether diol to polyether triol weight ratio ranges from about 2:3 to about 3:2.

28. The storage container combination according to claim 27 wherein the polyether diol and polyether triol each have a molecular weight ranging from about 1000 to about 8000, and wherein each consists essentially of either an ethylene ether linkage or a propylene ether linkage.

29. The storage container combination according to claim 28 wherein the supportive base comprises a multiple compartmentalized container having at least one compartment interfacing onto the insert.

30. The storage container combination according to claim 28 wherein the container combination comprises a rigid container equipped with multiple compartmentalized container beds bonded to the insert.

31. The storage container combination according to claim 30 wherein the storage container combination comprises a fishing tackle box.

32. The storage container combination according to claim 31 wherein the combination further includes fishing tackle immobilized within the fishing tackle box by said insert.

33. The storage container combination according to claim 32 wherein the fishing tackle includes multiple fishing lures stowed therein.

34. The storage container combination according to claim 28 wherein the supportive base comprises a flexible container.

35. The storage container combination according to claim 34 wherein the flexible container comprises a bag with handles.

36. The stowing container combination according to claim 14 wherein the stowing container combination comprises a hygienic container combination, and wherein the insert imparts sufficient hygienic properties to substantially inhibit microbial growth thereupon and sufficient adhesiveness to immobilize a hygienic item placed upon the insert.

37. The stowing container combination according to claim 36 wherein the hygienic container combination comprises an aseptic hygienic tray.

38. The storage container combination according to claim 26 wherein the reaction media comprises from about 25 to about 45 percent by weight epoxidized vegetable oil plasticizer, wherein the ester plasticizer has a molecular weight of less than 750, and wherein the reaction media further comprises an epoxidized vegetable oil plasticizer to ester plasticizer weight ratio ranging from about 1:1 to about 6:1.

39. The storage container combination according to claim 26 wherein the insert is chemically bonded to a surface area of the supportive base by the thermosetting of the reaction media upon the surface area.

40. The storage container combination according to claim 39 wherein the storage container combination comprises a hygienic container possessing antimicrobial properties imparted thereto by the insert.

41. The storage container combination according to claim 26 wherein the polyether diol and the polyether triol each comprise a sequenced oxyalkylene polyol grouping selected from the group consisting of a polyoxyethylene grouping and a polyoxypropylene grouping, wherein the polyether diol and the polyether triol each have a molecular weight ranging from about 3000 to about 6000, and wherein the epoxidized vegetable oil plasticizer consists essentially of an epoxidized soybean oil plasticizer and the ester plasticizer comprises dibutyl sebacate.

42. A method for preparing a container combination having an antipathogenic surface and sufficient adhesiveness to retain a stowed item at a stabilized stowed position and to cohesively release the stowed item from the stowed position upon the application of a sufficient force to overcome an adhesive attraction therebetween, said method comprising:
   a) providing a supportive base having a surface area of a sufficient size and a structural integrity to support the stowed item, and
   b) placing a cohesive and adhesive thermoset viscoelastomeric insert in an interfacing relationship to the surface area of the supportive base wherein the insert compositionally comprises a thermoset viscoelastomeric reaction product formed from a thermosetting reaction media comprising:
      a) about 10 to about 35 percent by weight polyether diol;
      b) about 25 to about 35 percent by weight polyether triol;
      c) about 4 to about 7 percent by weight isocyanate prepolymer; and
      d) about 20 to less than 50 percent by weight epoxidized vegetable oil plasticizer;
   wherein a reaction of the thermosetting reaction media is carried out in the presence of an effective amount of a catalyst for curing the thermosetting reaction media.

43. The method according to claim 42 further comprising initially coating the surface area of the supportive base with the thermosetting reaction media and thereafter allowing the thermosetting reaction media to cure to form the thermoset viscoelastomeric reaction product and thereby securely bonding the thermoset viscoelastomeric insert to the supportive base.

44. The method according to claim 42 wherein the reaction media comprises a diol to triol weight ratio ranging from about 7:13 to about 13:7, wherein the reaction media comprises a total plasticizer content ranging from about 20 to about 55 percent by weight, and wherein the reaction media further comprises an ester plasticizer in an amount ranging from about 2 to about 20 percent by weight of the reaction media.

45. The method according to claim 44 wherein the providing comprises the providing of a rigid container comprising multiple compartments, and wherein the placing comprises placing the thermoset viscoelastomeric insert in at least one of the compartments with the thermoset viscoelastomeric insert being adhesively engaged and releasably secured to the compartment.

46. The method according to claim 45 wherein the container comprises a fishing tackle box and the method includes adhesively engaging stowable fishing gear to the insert.

47. The method according to claim 44 wherein the container combination comprises a hygienic container combination fitted with an antimicrobial insert of said thermoset viscoelastomeric reaction product.

48. The method according to claim 42 wherein the placing includes a thermoset bonding of the reaction media onto the supportive base by an in situ curing of the reaction media to the surface area of the supportive base.

49. A thermoset viscoelastomeric reaction product having a desired degree of adhesiveness and cohesiveness towards stowable items placed in releasable contact therewith, said thermoset viscoelastomeric reaction product comprising a reaction product of a thermosetting reaction media comprising:
   a) from about 3 to about 8 percent by weight of an isocyanate prepolymer;
   b) from about 20 to about 40 percent by weight of a cross-linking polyoxyalkylene triol;
   c) from about 20 to about 40 percent by weight of a straight chain producing polyoxyalkylene diol;
   d) from 0 to less than 50 percent by weight of an epoxidized triglyceride plasticizer; and
   e) an effective amount of an ester plasticizer in excess of 5 percent by weight;
   wherein the thermosetting reaction media further comprises a polyoxyalkylene diol to polyoxyalkylene triol weight ratio of about 7:13 to about 13:7;
   wherein cross-linking is caused by the polymerization of the cross-linking polyoxyalkylene triols being separated by intervening straight chain bridging polymerizates provided by the polyoxyalkylene diols; and
   wherein the amount of epoxidized triglyceride plasticizer and ester plasticizer present in the thermosetting reaction media is sufficient to permit a formation of the thermoset viscoelastomeric reaction product in a desired reaction product form.

50. The thermoset viscoelastomeric reaction product according to claim 49 wherein the polyoxyalkylene triol and the polyoxyalkylene diol each have an alkylene grouping selected from the group consisting of an ethylene group or a propylene group.

51. The thermoset viscoelastomeric reaction product according to claim 50 wherein the molecular weight of the polyoxyalkylene diol and the polyoxyalkylene triol ranges from about 3000 to about 6000.

52. A thermoset viscoelastomeric reaction product obtained from a thermosetting reaction media comprising:
   a) from about 3 to about 10 percent by weight of an isocyanate prepolymer;
   b) from about 10 to about 40 percent by weight of a polyether triol having a molecular weight of at least 1000;
   c) from about 10 to about 35 percent by weight of a polyether diol having a molecular weight of at least 1000; and
   d) from about 20 to less than 50 percent by weight of a plasticizer,
   wherein the thermosetting reaction media further comprises a polyether diol to polyether triol weight ratio of 7:13 to 13:7; and
   wherein the polyether diol provides sufficient straight chain linkage to permit a loading of an effective amount of the plasticizer within the thermoset viscoelastomeric reaction product and to impart sufficient adhesiveness and cohesiveness to the thermoset viscoelastomeric reaction product so as to effectively adhesively engage a stowed item and to cohesively release the stowed item without leaving more than a nominal amount of the thermoset viscoelastomeric reaction product upon the stowed item released therefrom.

53. The thermoset viscoelastomeric reaction product according to claim 52 wherein the amount of the isocyanate prepolymer ranges from about 5 to about 8 percent by weight, wherein the amount of polyether triol ranges from about 20 to about 30 percent by weight with the polyether triol having a molecular weight ranging from about 4000 to about 8000, wherein the amount of polyether diol ranges from about 20 to about 30 percent by weight with the polyether diol having a molecular weight ranging from about 3000 to about 6000, and wherein the total plasticizer content ranges from about 25 to about 45 percent by weight.

54. The thermoset viscoelastomeric reaction product according to claim 53 wherein the plasticizer comprises an epoxidized vegetable oil plasticizer and an ester plasticizer having a molecular weight of less than 500, and wherein the thermosetting reaction media further comprises an epoxidized vegetable oil to ester plasticizer weight ratio ranging from about 1:1 to about 6:1.

55. The thermoset viscoelastomeric reaction product according to claim 52 wherein the thermosetting reaction media comprises:
a) about 10 to about 30 percent by weight of a polyether diol;
b) about 25 to about 35 percent by weight of a polyether triol;
c) about 4 to about 8 percent by weight of a diisocyanate prepolymer; and
d) about 42 to less than 50 percent by weight of an epoxidized vegetable oil;
wherein the thermosetting reaction media has been catalyzed in the presence of a catalytic amount of a thermosetting catalyst for curing the thermosetting reaction media.

56. The thermoset viscoelastomeric reaction product according to claim 55 wherein the weight ratio of polyether triol to the polyether diol and the amount of plasticizer impart a desired adhesiveness and cohesiveness to the reaction product.

57. The thermoset viscoelastomeric reaction product according to claim 55 wherein the polyether diol and the polyether triol each comprise either an ethylene or propylene linkage bridging between repetitive oxy groups, wherein the polyether diol has a molecular weight ranging from about 2000 to about 6000, and wherein the polyether triol has a molecular weight ranging from about 3000 to about 7000.

58. The thermoset viscoelastomeric reaction product according to claim 52 wherein the isocyanate prepolymer comprises diisocyanate in an amount ranging from about 5 to about 8 percent by weight, the polyether triol ranges from about 20 to about 30 percent by weight, the polyether diol ranges from about 20 to about 30 percent by weight and the total plasticizer weight ranges from about 25 to about 40 percent by weight, and wherein the diol to triol weight ratio ranges from about 2:3 to about 3:2.

59. The thermoset viscoelastomeric reaction product according to claim 58 wherein the diol to triol weight ratio and the amount of plasticizer within the thermosetting reaction media have been adjusted so as to provide a thermoset viscoelastomeric reaction product which exhibits a desired adhesiveness and cohesiveness.

60. A method for preparing an adhesive and cohesive thermoset viscoelastomeric reaction product article possessing sufficient adhesiveness to immobilize an adhesively adhered item thereto against displacement, said method comprising:
a) providing a substantially uniform uncured thermosetting reaction media admixture comprising an isocyanate prepolymer, an effective amount of a plasticizer containing less than 50 percent by weight of the thermosetting reaction media of an epoxidized triglyceride plasticizer, from about 35 to about 55 percent by weight polyols with said polyols consisting essentially of straight chain linking diols and cross-linking triols each having repetitive oxygen containing functional groups;
b) preforming the thermosetting reaction media admixture into a desired preformed article comprising a sufficient surface area to adhesively engage the adhered item; and
c) curing the preformed article to provide the thermoset viscoelastomeric reaction product article;
wherein thermosetting reaction media admixture further comprises a diol to triol weight ratio of about 7:13 to about 13:7; and
wherein the diol to triol weight ratio and the amount of plasticizer within the thermoset viscoelastomeric reaction product article are sufficient to stabilize the adhesively adhered item against displacement while providing sufficient cohesiveness so as to cohesively release the adhesively adhered item without leaving more than a nominal amount of polymeric residue upon the adhesively adhered item released therefrom.

61. The method according to claim 60 wherein the thermosetting reaction media admixture comprises:
a) about 10 to about 20 percent by weight of a polyether diol;
b) about 25 to about 35 percent of weight of a polyether triol;
c) about 4 to about 7 percent by weight of an diisocyanate prepolymer; and
d) about 42 to less than 50 percent by weight of an epoxidized vegetable oil plasticizer.

62. The method according to claim 61 wherein the polyether diol and the polyether triol each comprise a polyalkylene ether having an alkylene grouping of 2 to 3 carbon atoms with the polyether triol having a molecular weight ranging from about 3000 to about 7000 and the polyether diol having a molecular weight ranging from about 2000 to about 6000.

63. The method according to claim 60 wherein the preforming of the thermosetting reaction media admixture consists of preforming into a sheet or a film.

64. The method according to claim 63 wherein the sheet or the film has a thickness of less than 80 mil.

65. The method according to claim 60 wherein the preforming comprises preforming into a coating and chemically bonding the thermosetting reaction media admixture onto a flexible support.

66. The method according to claim 60 wherein the providing includes a thermosetting reaction media admixture comprising in excess of 5 percent by weight of an ester plasticizer having a molecular weight of less than 500, and wherein the preforming includes a depositing of the uncured thermosetting reaction media admixture upon an inert substrate and thereafter allowing the thermosetting reaction media admixture to cure to the desired thermoset viscoelastomeric reaction product article.

67. The method according to claim 61 wherein the thermosetting reaction media admixture is bonded to a hygienic device to impart aseptic properties to the hygienic device.

68. The method according to claim 60 wherein the preforming includes preforming of the thermosetting reaction media admixture into the form of an insertable insert and thereafter covering each exposed surface of the insertable insert with a protective covering.

69. The thermoset viscoelastomeric reaction product according to claim 13 wherein the thermoset viscoelastomeric reaction product comprises an insertable adhesive and cohesive insert having a protective covering disposed thereupon.

\* \* \* \* \*